United States Patent
Lin et al.

(10) Patent No.: US 11,171,789 B2
(45) Date of Patent: *Nov. 9, 2021

(54) SYSTEM AND METHOD FOR IMPLEMENTING A RESOLVER SERVICE FOR DECENTRALIZED IDENTIFIERS

(71) Applicant: ADVANCED NEW TECHNOLOGIES CO., LTD., Grand Cayman (KY)

(72) Inventors: Yuqi Lin, Hangzhou (CN); Yuan Chen, Hangzhou (CN); Renhui Yang, Hangzhou (CN); Jiawei Liu, Hangzhou (CN)

(73) Assignee: ADVANCED NEW TECHNOLOGIES CO., LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/129,372

(22) Filed: Dec. 21, 2020

(65) Prior Publication Data

US 2021/0111867 A1    Apr. 15, 2021

Related U.S. Application Data

(63) Continuation of application No. 16/846,192, filed on Apr. 10, 2020, now Pat. No. 10,938,551, which is a
(Continued)

(30) Foreign Application Priority Data

Jul. 2, 2019    (WO) ................ PCT/CN2019/094396

(51) Int. Cl.
*H04L 9/32*    (2006.01)
*H04L 9/06*    (2006.01)
(Continued)

(52) U.S. Cl.
CPC ............ *H04L 9/3242* (2013.01); *G06F 21/64* (2013.01); *H04L 9/0637* (2013.01); *H04L 9/30* (2013.01);
(Continued)

(58) Field of Classification Search
CPC . H04L 2209/38; H04L 9/3239; H04L 9/3247; H04L 63/00; H04L 63/102;
(Continued)

(56) References Cited

U.S. PATENT DOCUMENTS 9,992,022 B1    6/2018    Chapman et al.
10,057,243 B1    8/2018    Kumar et al.
(Continued)

FOREIGN PATENT DOCUMENTS

CN    107306183 A    10/2017
CN    107637015 A    1/2018
(Continued)

OTHER PUBLICATIONS

Mayrhofer et al., "The Decentralized Identifier (DID) in the DNS draft-mayrhofer-did-dns-01" Feb. 8, 2019 (Year: 2019).*
(Continued)

*Primary Examiner* — David R Lazaro

(57) ABSTRACT

Methods, systems, and apparatus, including computer programs encoded on computer storage media, for implementing a resolver service. One of the methods includes: obtaining, from a blockchain, event data for a plurality of blockchain transactions associated with a plurality of decentralized identifiers (DIDs); storing the event data in a database; receiving a request for information associated with the event data, wherein the request comprises one or more account identifiers; identifying one or more DIDs respectively corresponding to the one or more account identifiers based on pre-stored mapping relationships between the one
(Continued)

or more DIDs and the one or more account identifiers; and providing, from the database, event data for one or more blockchain transactions associated with the identified one or more DIDs.

20 Claims, 21 Drawing Sheets

Related U.S. Application Data continuation of application No. 16/734,972, filed on Jan. 6, 2020, now Pat. No. 10,700,851, which is a continuation of application No. PCT/CN2019/095303, filed on Jul. 9, 2019.

(51) Int. Cl.
    *G06F 21/64* (2013.01)
    *H04L 9/30* (2006.01)
    *H04L 29/06* (2006.01)

(52) U.S. Cl.
    CPC .......... *H04L 9/3234* (2013.01); *H04L 9/3239* (2013.01); *H04L 9/3247* (2013.01); *H04L 9/3271* (2013.01); *H04L 63/0876* (2013.01); *H04L 63/126* (2013.01); *H04L 2209/38* (2013.01)

(58) Field of Classification Search
    CPC . H04L 9/0877; H04L 9/3268; H04L 63/0815; H04L 63/0876; G06F 21/31
    See application file for complete search history.

(56) References Cited

U.S. PATENT DOCUMENTS

| | | | |
|---|---|---|---|
| 10,121,025 B1 | 11/2018 | Rice | |
| 10,127,378 B2 | 11/2018 | Toth | |
| 10,135,834 B1 | 11/2018 | Galebach et al. | |
| 10,135,835 B1 | 11/2018 | Kandel et al. | |
| 10,135,870 B2 | 11/2018 | Castinado et al. | |
| 10,142,333 B1 | 11/2018 | Griffin et al. | |
| 10,142,347 B2 | 11/2018 | Kurian | |
| 10,243,945 B1 | 3/2019 | Kruse et al. | |
| 10,298,396 B1 | 5/2019 | Kurani et al. | |
| 10,298,572 B2 | 5/2019 | Andrade | |
| 10,425,230 B1 | 9/2019 | Tang et al. | |
| 10,452,828 B1 | 10/2019 | Larimer et al. | |
| 10,454,906 B1 | 10/2019 | Sharfman et al. | |
| 10,454,927 B2 | 10/2019 | Oberhauser et al. | |
| 10,459,986 B2 | 10/2019 | Kneen et al. | |
| 10,506,104 B1 | 12/2019 | Shakeri | |
| 10,587,413 B1 | 3/2020 | Todd et al. | |
| 10,685,099 B2* | 6/2020 | Chen | G06F 21/45 |
| 10,693,629 B2 | 6/2020 | Guan et al. | |
| 10,700,851 B2* | 6/2020 | Lin | H04L 9/0877 |
| 10,728,042 B2* | 7/2020 | Li | G06F 16/953 |
| 10,824,701 B2* | 11/2020 | Chen | H04L 63/08 |
| 10,880,089 B2 | 12/2020 | Brown et al. | |
| 10,917,246 B2* | 2/2021 | Li | G06F 21/33 |
| 10,924,284 B2* | 2/2021 | Yang | H04L 9/0877 |
| 11,003,771 B2 | 5/2021 | Murdoch et al. | |
| 2003/0149781 A1 | 8/2003 | Yared et al. | |
| 2004/0049687 A1 | 3/2004 | Orsini et al. | |
| 2004/0158723 A1 | 8/2004 | Root | |
| 2006/0053296 A1 | 3/2006 | Busboom et al. | |
| 2006/0129817 A1 | 6/2006 | Borneman et al. | |
| 2006/0236382 A1 | 10/2006 | Hinton et al. | |
| 2007/0074021 A1 | 3/2007 | Smithies et al. | |
| 2007/0143860 A1 | 6/2007 | Hardt | |
| 2008/0065893 A1 | 3/2008 | Dutta et al. | |
| 2009/0126001 A1 | 5/2009 | Krantz et al. | |
| 2009/0254968 A1 | 10/2009 | Bussani et al. | |
| 2010/0199098 A1 | 8/2010 | King | |
| 2012/0008786 A1 | 1/2012 | Cronk et al. | |
| 2012/0284505 A1 | 11/2012 | Smith et al. | |
| 2013/0036458 A1 | 2/2013 | Liberman et al. | |
| 2013/0198516 A1 | 8/2013 | Fenton et al. | |
| 2013/0212393 A1 | 8/2013 | D'Souza | |
| 2013/0326596 A1 | 12/2013 | Hohlfeld et al. | |
| 2014/0089670 A1 | 3/2014 | Maletsky et al. | |
| 2014/0208119 A1 | 7/2014 | Chang et al. | |
| 2015/0006529 A1 | 1/2015 | Kneen et al. | |
| 2015/0288694 A1 | 10/2015 | Liebl, III et al. | |
| 2015/0356523 A1 | 12/2015 | Madden | |
| 2015/0381370 A1 | 12/2015 | Lam | |
| 2016/0055322 A1 | 2/2016 | Thomas | |
| 2016/0142211 A1 | 5/2016 | Metke et al. | |
| 2016/0316365 A1 | 10/2016 | Buhler et al. | |
| 2016/0359848 A1 | 12/2016 | Wilson et al. | |
| 2017/0048209 A1 | 2/2017 | Lohe et al. | |
| 2017/0109759 A1 | 4/2017 | Korb | |
| 2017/0140145 A1 | 5/2017 | Shah | |
| 2017/0177855 A1 | 6/2017 | Costa et al. | |
| 2017/0180128 A1 | 6/2017 | Lu | |
| 2017/0230353 A1 | 8/2017 | Kurian et al. | |
| 2017/0243208 A1 | 8/2017 | Kurian et al. | |
| 2017/0243287 A1 | 8/2017 | Johnsrud et al. | |
| 2017/0250972 A1 | 8/2017 | Ronda et al. | |
| 2017/0257358 A1 | 9/2017 | Ebrahimi et al. | |
| 2017/0310653 A1 | 10/2017 | Zhang | |
| 2017/0316390 A1 | 11/2017 | Smith et al. | |
| 2018/0006826 A1 | 1/2018 | Smith et al. | |
| 2018/0019879 A1 | 1/2018 | Kravitz et al. | |
| 2018/0026793 A1 | 1/2018 | Abt, Jr. et al. | |
| 2018/0054733 A1 | 2/2018 | Houseworth et al. | |
| 2018/0060496 A1* | 3/2018 | Bulleit | H04L 9/3239 |
| 2018/0101684 A1 | 4/2018 | Murphy et al. | |
| 2018/0114220 A1 | 4/2018 | Ekberg | |
| 2018/0144153 A1 | 5/2018 | Pead | |
| 2018/0165781 A1 | 6/2018 | Rodriguez et al. | |
| 2018/0176228 A1* | 6/2018 | He | H04L 63/105 |
| 2018/0191501 A1 | 7/2018 | Lindemann | |
| 2018/0191695 A1 | 7/2018 | Lindemann | |
| 2018/0204191 A1 | 7/2018 | Wilson et al. | |
| 2018/0205743 A1 | 7/2018 | McIver et al. | |
| 2018/0253539 A1 | 9/2018 | Minter et al. | |
| 2018/0262493 A1 | 9/2018 | Andrade | |
| 2018/0270065 A1 | 9/2018 | Brown et al. | |
| 2018/0285879 A1 | 10/2018 | Gadnis et al. | |
| 2018/0288033 A1 | 10/2018 | Kamal | |
| 2018/0294966 A1 | 10/2018 | Hyun et al. | |
| 2018/0308098 A1 | 10/2018 | Ebrahimi | |
| 2018/0343126 A1* | 11/2018 | Fallah | H04L 9/006 |
| 2018/0365201 A1 | 12/2018 | Hunn et al. | |
| 2018/0367310 A1 | 12/2018 | Leong et al. | |
| 2019/0013943 A1 | 1/2019 | Maim | |
| 2019/0035018 A1 | 1/2019 | Nolan et al. | |
| 2019/0036680 A1 | 1/2019 | Sundaresan | |
| 2019/0036692 A1 | 1/2019 | Sundaresan et al. | |
| 2019/0044917 A1 | 2/2019 | Mork et al. | |
| 2019/0044940 A1 | 2/2019 | Khalil et al. | |
| 2019/0050855 A1 | 2/2019 | Martino et al. | |
| 2019/0075102 A1 | 3/2019 | Kim et al. | |
| 2019/0089701 A1 | 3/2019 | Mercury et al. | |
| 2019/0108543 A1 | 4/2019 | Chan et al. | |
| 2019/0116188 A1 | 4/2019 | Praszczalek et al. | |
| 2019/0121813 A1 | 4/2019 | Galebach et al. | |
| 2019/0139047 A1 | 5/2019 | Ronnow et al. | |
| 2019/0141026 A1 | 5/2019 | Kshirsagar et al. | |
| 2019/0149334 A1 | 5/2019 | Van Der Velden | |
| 2019/0163896 A1* | 5/2019 | Balaraman | H04L 9/0637 |
| 2019/0164156 A1* | 5/2019 | Lindemann | H04L 9/3239 |
| 2019/0165943 A1 | 5/2019 | Chari et al. | |
| 2019/0179672 A1 | 6/2019 | Christidis et al. | |
| 2019/0180011 A1 | 6/2019 | Reinsberg et al. | |
| 2019/0180311 A1 | 6/2019 | Chan et al. | |
| 2019/0182035 A1 | 6/2019 | Chari et al. | |
| 2019/0222424 A1* | 7/2019 | Lindemann | H04L 63/0407 |
| 2019/0229909 A1 | 7/2019 | Patel et al. | |
| 2019/0229914 A1 | 7/2019 | Patel et al. | |
| 2019/0230073 A1 | 7/2019 | Patel et al. | |
| 2019/0230092 A1* | 7/2019 | Patel | H04L 9/0869 |

(56) References Cited

U.S. PATENT DOCUMENTS

| | | |
|---|---|---|
| 2019/0266576 A1 | 8/2019 | McCauley et al. |
| 2019/0268140 A1 | 8/2019 | Kandiraju et al. |
| 2019/0268162 A1 | 8/2019 | Sahagun et al. |
| 2019/0272548 A1 | 9/2019 | Korb |
| 2019/0273617 A1 | 9/2019 | Maher |
| 2019/0281028 A1 | 9/2019 | Gillan et al. |
| 2019/0289012 A1 | 9/2019 | Kandel et al. |
| 2019/0303552 A1 | 10/2019 | Houseworth et al. |
| 2019/0303587 A1 | 10/2019 | Hamel et al. |
| 2019/0303600 A1 | 10/2019 | Hamel et al. |
| 2019/0305949 A1 | 10/2019 | Hamel et al. |
| 2019/0305952 A1 | 10/2019 | Hamel et al. |
| 2019/0305954 A1 | 10/2019 | Hamel et al. |
| 2019/0306151 A1 | 10/2019 | Hamel et al. |
| 2019/0318338 A1 | 10/2019 | Verma et al. |
| 2019/0318399 A1 | 10/2019 | Davis et al. |
| 2019/0319939 A1 | 10/2019 | Hamel et al. |
| 2019/0327082 A1* | 10/2019 | Ow ..................... H04L 9/3213 |
| 2019/0327094 A1 | 10/2019 | Kan et al. |
| 2019/0333054 A1 | 10/2019 | Cona et al. |
| 2019/0334957 A1 | 10/2019 | Davis et al. |
| 2019/0340619 A1 | 11/2019 | Leong et al. |
| 2019/0342084 A1 | 11/2019 | Mehedy et al. |
| 2019/0342303 A1 | 11/2019 | Sun et al. |
| 2019/0349371 A1 | 11/2019 | Smith et al. |
| 2019/0349372 A1 | 11/2019 | Smith et al. |
| 2019/0363896 A1* | 11/2019 | Finlow-Bates ....... H04L 9/3239 |
| 2019/0379642 A1 | 12/2019 | Simons et al. |
| 2019/0386990 A1 | 12/2019 | Liu et al. |
| 2019/0394025 A1 | 12/2019 | Maim |
| 2020/0005292 A1* | 1/2020 | Mao .................... H04L 9/3247 |
| 2020/0007312 A1* | 1/2020 | Vouk ................... H04L 67/104 |
| 2020/0026834 A1 | 1/2020 | Vimadalal et al. |
| 2020/0028688 A1 | 1/2020 | Takada |
| 2020/0036707 A1* | 1/2020 | Callahan .............. H04L 9/3231 |
| 2020/0044831 A1 | 2/2020 | Soundararajan et al. |
| 2020/0044848 A1 | 2/2020 | Chari et al. |
| 2020/0067697 A1 | 2/2020 | Puddu et al. |
| 2020/0067907 A1 | 2/2020 | Avetisov et al. |
| 2020/0076601 A1* | 3/2020 | Tabrizi ............... G06Q 20/3829 |
| 2020/0076602 A1 | 3/2020 | Redpath et al. |
| 2020/0092107 A1 | 3/2020 | Cole |
| 2020/0092292 A1* | 3/2020 | Patel ....................... H04L 9/32 |
| 2020/0099513 A1 | 3/2020 | Angelo et al. |
| 2020/0104296 A1 | 4/2020 | Hunn et al. |
| 2020/0111118 A1 | 4/2020 | Patel et al. |
| 2020/0127828 A1* | 4/2020 | Liu ..................... H04L 9/30 |
| 2020/0127845 A1* | 4/2020 | Yang ................... H04L 9/0643 |
| 2020/0127847 A1* | 4/2020 | Yang ................... H04L 63/0815 |
| 2020/0137064 A1 | 4/2020 | Wu et al. |
| 2020/0143019 A1* | 5/2020 | Chen .................. G06Q 20/3829 |
| 2020/0145196 A1* | 5/2020 | Lin ..................... G06F 21/64 |
| 2020/0145209 A1* | 5/2020 | Yang ................... H04L 9/3263 |
| 2020/0145223 A1* | 5/2020 | Yang ................... H04L 63/08 |
| 2020/0145229 A1* | 5/2020 | Li ....................... H04L 9/30 |
| 2020/0153606 A1* | 5/2020 | Li ....................... H04L 63/08 |
| 2020/0153639 A1* | 5/2020 | Yang ................... H04L 9/0877 |
| 2020/0162244 A1 | 5/2020 | Wang |
| 2020/0177373 A1 | 6/2020 | Komandur et al. |
| 2020/0184085 A1 | 6/2020 | Korten et al. |
| 2020/0211409 A1 | 7/2020 | Latorre et al. |
| 2020/0220728 A1 | 7/2020 | Ardashev et al. |
| 2020/0242221 A1* | 7/2020 | Chen ................... H04L 63/08 |
| 2020/0244439 A1* | 7/2020 | Lin ..................... H04L 9/0877 |
| 2020/0252206 A1 | 8/2020 | Yeung et al. |
| 2020/0252210 A1 | 8/2020 | Sharfman et al. |
| 2020/0304315 A1* | 9/2020 | Li ....................... H04L 9/3239 |
| 2020/0311094 A1* | 10/2020 | Opferman ............ G06F 16/254 |
| 2020/0374132 A1 | 11/2020 | Lobban et al. |
| 2020/0394654 A1 | 12/2020 | Concannon et al. |
| 2020/0403795 A1 | 12/2020 | Murdoch et al. |
| 2020/0403805 A1* | 12/2020 | Steele .................. G06F 21/602 |
| 2021/0006410 A1 | 1/2021 | Uhr et al. |
| 2021/0012013 A1 | 1/2021 | Gourisetti et al. |
| 2021/0051025 A1* | 2/2021 | Li ........................ H04L 9/3247 |
| 2021/0099438 A1 | 4/2021 | Kurian |

FOREIGN PATENT DOCUMENTS

| | | |
|---|---|---|
| CN | 108833114 A | 11/2018 |
| CN | 109327456 A | 2/2019 |
| CN | 109493082 A | 3/2019 |
| CN | 109918878 A | 6/2019 |
| CN | 109918942 A | 6/2019 |
| CN | 109922077 A | 6/2019 |
| CN | 109936569 A | 6/2019 |
| CN | 109936570 A | 6/2019 |
| TW | 201447635 A | 12/2014 |
| TW | 201926111 A | 7/2019 |
| WO | 2018047085 A1 | 3/2018 |
| WO | 2019014592 A1 | 1/2019 |
| WO | 2019/104323 A1 | 5/2019 |
| WO | 2019/179537 A2 | 9/2019 |
| WO | WO-2019179537 A2 * | 9/2019 ............. G06F 21/31 |
| WO | 2019/191216 A1 | 10/2019 |
| WO | WO-2019191216 A1 * | 10/2019 ........... H04L 9/3247 |
| WO | 2019/228556 A2 | 12/2019 |

OTHER PUBLICATIONS

Notice of Allowance for U.S. Appl. No. 17/086,832 dated Jan. 25, 2021.
Written Opinion and International Search Report for PCT Application No. PCT/CN2019/103758 made available to public on Jan. 7, 2021.
Written Opinion and I nternational Search Report for PCT Application No. PCT/CN2019/103798 made avilable to public on Jan. 7, 2021.
Search Report for European Application No. 19771466.0 dated Nov. 6, 2020.
Search Report for European Application No. 19771295.3 dated Aug. 24, 2020.
Search Report for European Application No. 19772514.6 dated Sep. 7, 2020.
Search Report for European Application No. 19772156.6 dated Sep. 7, 2020.
Written Opinion and International Search Report for PCT Application No. PCT/CN2019/094427 dated Apr. 7, 2020.
Written Opinion and International Search Report for PCT Application No. PCT/CN2019/094396 dated Apr. 10, 2020.
Written Opinion and International Search Report for PCT Application No. PCT/CN2019/103791 dated Apr. 1, 2020.
Written Opinion and International Search Report for PCT Application No. PCT/CN2019/103780 dated Apr. 3, 2020.
Written Opinion and International Search Report for PCT Application No. PCT/CN2019/103730 dated Mar. 26, 2020.
Written Opinion and International Search Report for PCT Application No. PCT/CN2019/095303 dated Mar. 26, 2020.
Written Opinion and International Search Report for PCT Application No. PCT/CN2019/094409 dated Mar. 27, 2020.
Notice of Allowance for U.S. Appl. No. 16/912,325, dated Aug. 4, 2020.
Notice of Allowance for U.S. Appl. No. 16/719,026, dated Sep. 17, 2020.
Notice of Allowance for U.S. Appl. No. 16/718,937, dated Jul. 20, 2020.
Notice of Allowance for U.S. Appl. No. 16/846,150, dated Jun. 23, 2020.
Notice of Allowance for U.S. Appl. No. 16/737,806, dated Jun. 17, 2020.
Notice of Allowance for U.S. Appl. No. 16/735,538, dated Mar. 4, 2020.
Notice of Allowance for U.S. Appl. No. 16/737,797 dated Mar. 18, 2020.
Notice of Allowance for U.S. Appl. No. 16/734,972 dated Feb. 24, 2020.

(56) References Cited

OTHER PUBLICATIONS

Non-Final Office Action for U.S. Appl. No. 16/718,984, dated Aug. 21, 2020.
Non-Final Office Action for U.S. Appl. No. 16/719,026, dated Apr. 17, 2020.
Non-Final Office Action for U.S. Appl. No. 16/718,937, dated Mar. 13, 2020.
Non-Final Office Action for U.S. Appl. No. 16/735,018, dated Mar. 23, 2020.
Final Office Action for U.S. Appl. No. 16/718,984, dated Dec. 24, 2020.
Pre-interview First Office Action for U.S. Appl. No. 16/737,813 dated Apr. 2, 2020.
A Primer for Decentralized Identifiers, published in 2019, available at https://w3c-ccg.github.io/didprimer/, 3 pages.
Allen et al., "Decentralized Identifiers (DIDs) v0.9", W3C, Jan. 2018, pp. 1-39.
Anonymous, "education/introduction-to-hyperledger-indy.md", https://github.com/hyperledger/education/blob/master/LFS171x/docs/introduction-to-hyperledger-indy.md, retrieved on May 25, 2020.
Aydar et al., "Towards a blockchain based digital identity verification, record attstation and record sharing system," Jun. 24, 2019.
Barbir, Abbie. "Updated text for X.dlt-sec, Security considerations for using DLT data in Identity Management; C-0471", ITU-T Draft, International Telecommunication Union, Jan. 3, 2019.
Barker et al., "A Framework for Designing Cryptographic Key Management Systems", N $1^{st}$ Special Publication 800-130, N $1^{st}$, Aug. 2003, pp. 1-120.
Decentralized Identifiers (DIDs) v1.0, published Dec. 2019, available at https://www.w3.org/TR/2019/WD-did-core-20191107/, 60 pages.
De Rooij, "Verifiable Claims for Digital Identity", VX Company, Aug. 2018, p. 1-17.
Duffy et al., "Use Cases for Decentralized Identifiers", W3C Draft Community Group Report, Feb. 2019, pp. 1-12.
Hardman, Daniel. "How DIDs, Keys, Credentials, and Agents Work in Sovrin", sovrin.org, Apr. 2018, pp. 1-7.
IEEE, "Decentralized Identity", Sep. 19, 2018.
Lee, Sunny et al., "Verifiable Claims Task Force Use Cases", Apr. 3, 2018.
Lim et al, "Blockchain Technology the Identity Management and Authentication Service Disruptor: A Survey", International Journal on Advanced Science Engineering Information Technology, 2018, vol. 8, No. 4-2.
Lindell, "Fast Secure Two-Party ECDSA Signing," Annual International Cryptology Conference. Springer, Cham, Jul. 29, 2017, pp. 613-644.
Makoto, Takemiya et al., "Sora Identity: Secure, Digital Identity on the Blockchain", IEEE, Jul. 23, 2018.
Microsoft, "Decentralized Identity, Own and Control your Identity", 2018, retrieved from https://query.prod.cms.rt.microsoft.com/cms/api/am/binary/RE2DjfY obtained on Apr. 11, 2020.
Muhle et al., "A survey on essential components of a self-sovereign identity" Elsevier Computer Science Review 30, 2018, pp. 80-86.
Othman et al., "The Horcrux Protocol: A Method for Decentralized Biometric based Self-sovereign Identity," IJCNN, Oct. 5, 2018.
Piper et al., "Cryptography, A Very Short Introduction", Oxford University Press, 2002, p. 96-99.
Reed et al., "DKMS (Decentralized Key Management System) Design and Architecture V4", Mar. 29, 2019, https://github.com/hypertedger/indy-hipe/blob/master/design/dkms-v4.md, accessed Dec. 16, 2020, pp. 1-69.
Reza, Soltani et al., "A New Approach to Client Onboarding Using Self-Sovereign Identity and Distributed Ledger", Jul. 30, 2018 IEEE.
Sovrin Foundation, "Sovrin: A Protocol and Token for Self-Sovereign Identity and Decentralized Trust", White Paper, Jan. 2018, pp. 1-42.
Sporny et al., "Verifiable Claims Data Model and Representations 1.0", May 1, 2017.
Sporny et al., "Verifiable Claims Use Cases", W3C Working Group Note, Jul. 2017, W3C, pp. 1-17.
Sporny et al., "A Decentralized Hashtable for the Web", W3C Draft Community Group Report, Mar. 2018, W3C, pp. 1-13.
Sporny et al., "A Primer for Decentralized Identifiers", W3C Draft Community Group Report, Jan. 2019, W3C, pp. 1-8.
Tobin, Andrew., "Sovrin: What Goes on the Ledger?", Evernym/Sovrin Foundation, Sep. 2018, p. 1-11.
Windley, Phillip., "How Sovrin Works", Sovrin Foundation, Oct. 3, 2016, pp. 1-10.
Zheng et al., "Blockchain challenges and opportunities: a survey", International Journal of Web and Grid Services, vol. 14, No. 4, Oct. 26, 2018.
Non-Final Office Action for U.S. Appl. No. 17/105,734 dated Mar. 12, 2021.
Non-Final Office Action for U.S. Appl. No. 17/156,412 dated Apr. 16, 2021.
Nate Otto and Kim Hamilton Duffy, "Open Badges are Verifiable Credentials", Jul. 9, 2018, obtained online from <https://github.com/WebOfT rusll nfo/rwot6-santabarbara/blob/master/final-documents/open-badges-are-verifiable-credentials.md>, retrieved on Apr. 10, 2021.
Search Report for Taiwanese Application No. 109109956 dated Nov. 9, 2020.
Search Report for Taiwanese Application No. 109110468 dated Jan. 18, 2021.
Search Report for Taiwanese Application No. 109110467 dated Feb. 20, 2021.
Non-Final Office Action for U.S. Appl. No. 17/173,374 dated May 19, 2021.
Notice of Allowance for U.S. Appl. No. 17/105,734 dated Jun. 30, 2021.
"ShoCard Whitepaper—Identity Management Verified Using the Blockchain", retrieved from the Internet, https://shocard .com/wp-content/uploads/2019/02/ShoCard-Whitepaper-2019 .pdf, 2019.
Final Office Action for U.S. Appl. No. 17/156,412 dated Jul. 28, 2021.

* cited by examiner

SYSTEM AND METHOD FOR IMPLEMENTING A RESOLVER SERVICE FOR DECENTRALIZED IDENTIFIERS

CROSS REFERENCE TO RELATED APPLICATIONS

This application is a continuation application of U.S. patent application Ser. No. 16/846,192, filed Apr. 10, 2020, which is a continuation application of Ser. No. 16/734,972, filed Jan. 6, 2020, which is a continuation application of International Application No. PCT/CN2019/095303, filed with the China National Intellectual Property Administration (CNIPA) on Jul. 9, 2019. International Application No. PCT/CN2019/095303 claims priority to and benefits of International Application No. PCT/CN2019/094396, filed with the CNIPA on Jul. 2, 2019. The entire contents of all of the above-identified applications are incorporated herein by reference.

TECHNICAL FIELD

This application generally relates to methods and devices for managing decentralized identifiers and verifiable claims based on blockchain technology.

BACKGROUND

Traditional identity management systems are based on centralized authorities such as corporate directory services, certificate authorities, or domain name registries. Each of the centralized authorities may serve as a root of trust that provides credibility to the identity it endorses. For such systems, data associated with the identities is often stored in centralized databases, if not traditional information storage media. The maintenance of identity of each person or entity is under the control of the centralized authorities. Given its nature, traditional identity management systems are subject to security risks suffered by each of the centralized authorities and provide inefficient mechanisms for the aggregation of identities or credentials provided by different centralized authorities. In such systems, individual entities or identity owners are often neither free to choose the root of trust nor in control over their own identities or credentials. Authentication and verification of their identities often prove to be inefficient.

Blockchain technology provides the opportunity to establish a trustworthy decentralized system that does not require trust in each member of the system. Blockchain provides data storage in a decentralized fashion by keeping the data in a series of data blocks having precedence relationship between each other. The chain of blocks is maintained and updated by a network of blockchain nodes, which are also responsible for validating data under a consensus scheme. The stored data may include many data types, such as financial transactions among parties, historical access information, etc.

Many blockchains (e.g., the Ethereum blockchain) have enabled blockchain contracts (also referred to as smart contracts) that are executed through blockchain transactions. Blockchain transactions are signed messages originated by externally owned accounts (e.g., blockchain accounts), transmitted by the blockchain network, and recorded in the blockchain. The blockchain contracts may be written to achieve various functions, such as adding data to blockchain accounts, changing data in the blockchain, etc. Thus, the blockchain can be maintained and updated by executing various blockchain transactions.

Blockchain technology provides the means for managing a root of trust without centralized authority. However, identity management systems built based on blockchain often present substantive technical barriers for the regular user by requiring storage of a blockchain ledger, capabilities to create and execute blockchain transactions and contracts, or participation in the consensus scheme of the blockchain. An identity holder may be required to keep important identity credentials such as cryptographic keys, which may subject the identity holder to the risk of loss of identity when such identity credentials are compromised. Furthermore, for business entities with the needs to manage identities for a large number of users, such identity management systems often prove to be inefficient and user-unfriendly. Mapping between identities managed by such an identity management system and accounts or service IDs kept by business entities are often difficult to maintain. Finally, such identity management systems often require frequent access to and interaction with the blockchain network, which may be costly and resource consuming.

SUMMARY

Various embodiments of the specification include, but are not limited to, systems, methods, and non-transitory computer readable media for implementing a resolver service.

According to some embodiments, a computer-implemented method for implementing a resolver service comprises obtaining event data from a blockchain, wherein the event data comprises a plurality of updates associated with a plurality of decentralized identifier (DID) documents stored on the blockchain, and storing the event data in a database. The method further comprises receiving a request for information associated with the event data and providing information about one or more updates associated with one or more of the DID documents in response to the request.

In some embodiments, the event data further comprises a plurality of updates associated with a plurality of verifiable claims (VCs).

In some embodiments, the obtaining event data comprises periodically accessing an up-to-date version of the blockchain.

In some embodiments, the obtaining event data comprises obtaining a current height of the blockchain, comparing the obtained current height of the blockchain with a maximum height in the blockchain that data currently stored in the database corresponds to, and obtaining a plurality of blocks from the blockchain, wherein each of the obtained blocks corresponds to a height in the blockchain greater than the maximum height.

In some embodiments, the obtaining event data further comprises searching, in the obtained blocks, for transactions involving one or more blockchain contracts associated with DIDs or VCs and collecting one or more inputs and outputs associated with the one or more blockchain contracts.

In some embodiments, the providing information about one or more updates comprises sending the information to an online agent configured to manage DIDs or VCs for a plurality of users.

In some embodiments, the receiving a request for information associated with the event data comprises receiving the request from an entity, wherein the request comprises one or more account identifiers. The providing information about one or more updates comprises identifying one or more DIDs based on pre-stored mapping relationships between a plurality of account identifiers and a plurality of DIDs and sending information associated with the identified one or more DIDs to the entity.

In some embodiments, the method further comprises receiving a request for creating a DID and sending one or more blockchain transactions for creating the DID and for adding a DID document associated with the DID to a blockchain node for execution.

In some embodiments, the method further comprises receiving a request for updating a DID document and sending a blockchain transaction for updating the DID document to a blockchain node for execution.

In some embodiments, the method further comprises receiving a query for a DID document, the query comprising a DID, and sending a blockchain transaction for identifying the DID document based on the DID to a blockchain node for execution.

In some embodiments, the method further comprises receiving a query for a public key associated with a DID and sending, to a blockchain node for execution, a blockchain transaction for accessing a DID document containing the public key based on the DID.

In some embodiments, the method further comprises receiving a query for information associated with a VC, the query comprising one or more identifiers for the VC and sending, to a blockchain node for execution, a blockchain transaction for accessing the information associated with the VC based on the one or more identifiers.

According to other embodiments, a system for implementing a resolver service comprises one or more processors and one or more computer-readable memories coupled to the one or more processors and having instructions stored thereon that are executable by the one or more processors to perform the method of any of the preceding embodiments.

According to yet other embodiments, a non-transitory computer-readable storage medium is configured with instructions executable by one or more processors to cause the one or more processors to perform the method of any of the preceding embodiments.

According to still other embodiments, an apparatus for implementing a resolver service comprises a plurality of modules for performing the method of any of the preceding embodiments.

According to some embodiments, a system for implementing a resolver service comprises one or more processors and one or more computer-readable memories coupled to the one or more processors and having instructions stored thereon that are executable by the one or more processors to perform operations comprising obtaining event data from a blockchain, wherein the event data comprises a plurality of updates associated with a plurality of decentralized identifier (DID) documents stored on the blockchain, and storing the event data in a database. The operations further comprise receiving a request for information associated with the event data and providing information about one or more updates associated with one or more of the DID documents in response to the request.

According to other embodiments, a non-transitory computer-readable storage medium is configured with instructions executable by one or more processors to cause the one or more processors to perform operations comprising obtaining event data from a blockchain, wherein the event data comprises a plurality of updates associated with a plurality of decentralized identifier (DID) documents stored on the blockchain, and storing the event data in a database. The operations further comprise receiving a request for information associated with the event data and providing information about one or more updates associated with one or more of the DID documents in response to the request.

According to yet other embodiments, an apparatus for implementing a resolver service comprises an obtaining module for obtaining event data from a blockchain, wherein the event data comprises a plurality of updates associated with a plurality of decentralized identifier (DID) documents stored on the blockchain; a storing module for storing the event data in a database; a receiving module for receiving a request for information associated with the event data; and a providing module for providing information about one or more updates associated with one or more of the DID documents in response to the request.

Embodiments disclosed herein have one or more technical effects. In some embodiments, a resolver service for blockchain-based decentralized identity management integrates the capabilities of executing DID methods, creating blockchain operations, and collecting data from the blockchain, and makes such capabilities accessible to external systems or applications via API interfaces. This allows flexible control of operations related to decentralized identity management and convenient access to information associated with decentralized identities using programming languages or protocols other than those required by the blockchain. In other embodiments, the resolver service provides interfaces and automated software solutions for an entity to manage identities on behalf of a plurality of other entities. The resolver service is also configured to leverage mapping information between decentralized identities and business accounts or service IDs. This facilitates effective synchronization of data between a blockchain storing information about decentralized identities and external databases storing information about local accounts corresponding to the decentralized identities. In yet other embodiments, the resolver service aggregates and executes certain transactions that would otherwise be executed by a blockchain system for decentralized identity management and categorizes and filters large amounts of data obtained from the blockchain system. This reduces the cost and resource consumption related to piecemeal execution of blockchain transactions and data queries.

These and other features of the systems, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as limiting.

DETAILED DESCRIPTION

Figure 1:
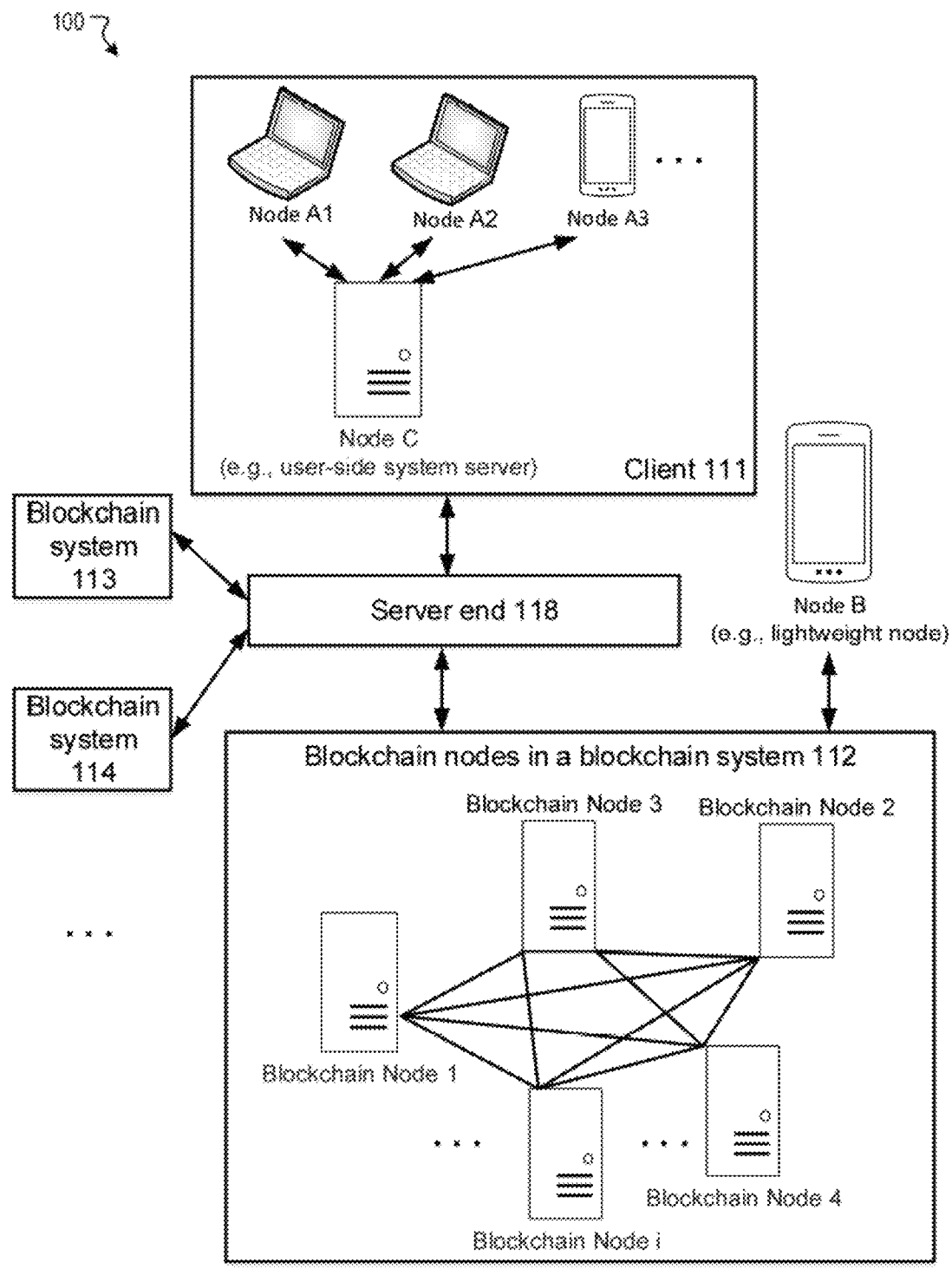
FIG. 1 illustrates a network environment associated with a blockchain in accordance with some embodiments.

Embodiments described herein provide methods, systems, and apparatus associated with an ecosystem for decentralized identity management that may provide unique and verifiable identities to entities. A decentralized identifier (DID) for an entity may allow the entity to obtain full control over its identity as well as information associated with the identity. Verifiable claims (VCs) may allow for authorizations, endorsements, and acknowledgements among different entities. In a business setting, a service or product provider may use its customers' DIDs and VCs to identify and authenticate the customers and to provide services or products accordingly.

In some embodiments, a DID may be a unique identifier indicating a mapping relationship between a real-world entity and an online identity. The DID may comprise a URL scheme identifier, an identifier for a DID method, and a DID method-specific identifier. Each DID may point to a corresponding DID document. The DID document may comprise descriptive text in a preset format (e.g., JSON-LD) about the DID and the owner of the DID. The DID may serve as a uniform resource identifier (URI) for locating the DID document. The DID document may comprise various properties such as contexts, DID subject, public keys, authentication, authorization and delegation, service endpoints, creation, updates, proof, extensibility, other suitable properties, or any combination thereof. The DID document may define or point to resources defining a plurality of operations that can be performed with respect to the DID.

In some embodiments, a VC may provide verifiable online information about an entity's qualities, characteristics, relationships, and other relevant information. A VC may comprise descriptive text in a preset format (e.g., JSON-LD) that describes one or more declarations regarding a DID (e.g., age of the owner of the DID, educational background of the owner of the DID) and an endorsement of an entity for the declaration. A VC may comprise various properties such as contexts, identifiers, types, credential subject, issuer, issuance date, proofs, expiration, status, presentations, other suitable properties, or any combination thereof. The VC may specify a type of its claim, which may indicate a structure of the claim. This may facilitate automatic processing by the VC issuer and VC verifiers.

Owners of DIDs may participate in the identity management system in different roles. For example, an individual may desire to use the services provided by a business entity, which requires proof that the individual is over 18 years of age. The individual may be an owner of a DID and may request a VC issued by a government agency that provides verification of citizens' ages. The business entity may verify the VC to ascertain that the individual meets the age requirement. In this scenario, the individual may be a DID owner and a VC holder; the government agency may be a VC issuer, and the business entity may be a VC verifier. As another example, a user may issue a VC to a first business allowing the first business to use the user's data stored by a second business. In this case, the user may act as a VC issuer; the first business may act as a DID owner and VC holder; the second business may act as a VC verifier.

Some embodiments integrate various components, such as blockchain networks, cloud applications, agent services, resolver services, user applications, application programing interface (API) services, key management systems (KMS), and other suitable components, to enable functionalities such as creation and authentication of DIDs and issuance and verification of VCs. In some embodiments, an online platform integrating one or more of these components may facilitate a business entity in smoothly creating DIDs and issuing VCs for its users. The business may interact with the online platform via one or more API interfaces and trust a plurality of cryptographic keys to the online platform. The online platform may offer agent services that perform various operations related to DIDs and VCs on behalf of the business entity and/or its users. Alternatively, the online platform may provide SDKs that can be integrated into applications of the business entity for directly performing operations related to DIDs and VCs.

In some embodiments, a resolver or resolver service may comprise a software component for managing relationships among DIDs, DID documents, or VCs. The resolver may comprise an API designed to accept requests for DID lookups and may execute the corresponding DID method to retrieve the authoritative DID document. The resolver may further interface with a blockchain and perform various operations such as creating a new DID or updating a DID document. Furthermore, the resolver may obtain various information related to DIDs and VCs from the blockchain and provide the information to other systems or components described herein.

FIG. 1 illustrates a network environment associated with a blockchain in accordance with some embodiments. As shown, in the environment 100, a client 111 may couple to a server end 118, and the server end 118 and a Node B may couple to a blockchain system 112 through various communication networks. Similarly, the server end 118 may optionally couple to more blockchain systems similar to the blockchain system 112 such as blockchain system 113, blockchain system 114, etc. Each blockchain system may maintain one or more blockchains.

In some embodiments, the client 111 may comprise one or more servers (e.g., Node C) and one or more other computing devices (e.g., Node A1, Node A2, Node A3). Node A1, Node A2, and Node A3 may couple to Node C. In some embodiments, Node C may be implemented by an entity (e.g., website, mobile phone Application, organization, company, enterprise), which has various local accounts (e.g., local accounts assessed from Node A1, Node A2, Node A3). For example, a mobile phone Application may have millions of end-users accessing the Application's server from respective user accounts. The Application's server may correspondingly store millions of user accounts. The components of the client 111 and their arrangement may have many other configurations.

In some embodiments, Node B may include a lightweight node. A lightweight node may not download the complete blockchain, but may instead just download the block headers to validate the authenticity of the blockchain transactions. Lightweight nodes may be served by and effectively dependent on full nodes (e.g., blockchain nodes in the blockchain system 112) to access more functions of the blockchain. The lightweight nodes may be implemented in electronic devices such as laptops, mobile phones, and the like by installing an appropriate software.

In some embodiments, there may be many more clients coupled to the server end 118 similar to client 111. The server end 118 may provide Blockchain-as-a-Service (BaaS) and be referred to as a BaaS cloud. In one embodiment, BaaS is a cloud service model in which clients or developers outsource behind-the-scenes aspects of a web or mobile application. BaaS may provide pre-written software for activities that take place on blockchains, such as user authentication, database management, and remote updating. The BaaS cloud may be implemented in a server, server cluster, or other devices. In one embodiment, the BaaS cloud provides an enterprise-level platform service based on blockchain technologies. This service may help clients to build a secure and stable blockchain environment as well as manage the deployment, operation, maintenance, and development of blockchain easily. Based on the abundant security strategies and multi-tenant isolation of cloud, the BaaS cloud can provide advanced security protection using chip encryption technologies. Based on highly reliable data storage, this service may provide end-to-end and highly available services that can scale up quickly without interruption. The BaaS cloud can provide native support for standard blockchain applications and data.

In some embodiments, the blockchain system 112 may comprise a plurality of blockchain nodes (e.g., Blockchain Node 1, Blockchain Node 2, Blockchain Node 3, Blockchain Node 4, Blockchain Node i, etc.) that maintain one or more blockchains (e.g., public blockchain, private blockchain, consortium blockchain). Other blockchain systems (e.g., blockchain system 113, blockchain system 114) may comprise similar arrangements of blockchain nodes maintaining other blockchains. Each blockchain node may be found in one or more blockchain systems. The blockchain nodes of each blockchain system may maintain one or more blockchains. The blockchain nodes may include full nodes. Full nodes may download every block and blockchain transaction and check them against the blockchain's consensus rules. The blockchain nodes may form a network (e.g., peer-to-peer network) with one blockchain node communicating with another. The order and the number of the blockchain nodes as shown are merely examples for illustration. The blockchain nodes may be implemented in servers, computers, etc. For example, each blockchain node may be implemented in a server or a cluster of servers. The cluster of servers may employ load balancing. Each blockchain node may correspond to one or more physical hardware devices or virtual devices coupled together via various types of communication methods such as TCP/IP. Depending on the classifications, the blockchain nodes may also be referred to as full nodes, Geth nodes, consensus nodes, etc.

In the environment 100, each of the nodes and devices may be installed with appropriate software (e.g., application program interface) and/or hardware (e.g., wires, wireless connections) to access other devices of the environment 100. In general, the nodes and devices may be able to communicate with one another through one or more wired or wireless networks (e.g., the Internet) through which data can be communicated. Each of the nodes and devices may include one or more processors and one or more memories coupled to the one or more processors. The memories may be non-transitory and computer-readable and configured with instructions executable by one or more processors to cause the one or more processors to perform operations described herein. The instructions may be stored in the memories or downloaded over a communications network without necessarily being stored in the memories. Although the nodes and devices are shown as separate components in this figure, it will be appreciated that these nodes and devices can be implemented as single devices or multiple devices coupled together. For example, Node B may be alternatively integrated into Blockchain Node 2.

The devices such as Node A1, Node A2, Node A3, Node B, and Node C may be installed with an appropriate blockchain software to create blockchain accounts, and initiate, forward, or access blockchain transactions. The term "blockchain transaction" may refer to a unit of task executed in a blockchain system and recorded in the blockchain. For example, Node A1 may access the blockchain through communications with Node C, the server end 118, and Blockchain Node 1, and Node B may access the blockchain through communications with Blockchain Node 2. In some embodiments, Node A1 may submit a blockchain account creation request to Node C. Node C may forward the request and other similar requests to the server end 118. The server end 118 may accordingly create blockchain accounts.

In some embodiments, after receiving a blockchain transaction request of an unconfirmed blockchain transaction, a recipient blockchain node may perform some preliminary verification of the blockchain transaction. For example, Blockchain Node 1 may perform the preliminary verification after receiving a blockchain transaction from Node C. Once verified, the blockchain transaction may be stored in the pool database of the recipient blockchain node (e.g., Blockchain Node 1), which may also forward the blockchain transaction to one or more other blockchain nodes (e.g., Blockchain Node 3, Blockchain Node 4). As each blockchain node may comprise or couple to a memory, the pool database may be respectively stored in the memories of the blockchain nodes. The pool database may store a plurality of blockchain transactions submitted by the one or more client devices. After receiving the blockchain transaction, the one or more other blockchain nodes may repeat the process done by the recipient blockchain node.

Each blockchain node may select some of the blockchain transactions from the pool according to its preference and form them into a proposed new block for the blockchain. The blockchain node may perform "mining" of the proposed new block by devoting computing power to solve complex mathematical problems. If the blockchain transaction involves a blockchain contract, the blockchain nodes may execute the blockchain contract locally in respective virtual machines (VMs). To handle the blockchain contracts, each blockchain node of the blockchain network may run a corresponding VM and executes the same instructions in the blockchain contract. A VM is a software emulation of a computer system based on computer architectures and provide functionality of a physical computer. VM in the blockchain context can be understood as a system designed to operate as a runtime environment for blockchain contracts.

A certain blockchain node that successfully mines the proposed new block of blockchain transactions in accordance with consensus rules may pack the new block into its local copy of the blockchain and multicast the results to other blockchain nodes. The certain blockchain node may be a blockchain node that has first successfully completed the verification, that has obtained a verification privilege, or that has been chosen based on another consensus rule, etc. Then, the other blockchain nodes may follow the same order of execution performed by the certain blockchain node to locally execute the blockchain transactions in the new block, verify the execution results with one another (e.g., by performing hash calculations), and synchronize their copies of the blockchain with that of the certain blockchain node. By updating their local copies of the blockchain, the other blockchain nodes may similarly write such information in the blockchain transaction into respective local memories. As such, the blockchain contract can be deployed on the blockchain. If the verification fails at some point, the blockchain transaction is rejected.

The deployed blockchain contract may have an address, according to which the deployed contract can be accessed. A blockchain node may invoke the deployed blockchain contract by inputting certain parameters to the blockchain contract. In one embodiment, Node C or Node B may request to invoke the deployed blockchain contract to perform various operations. For example, data stored in the deployed blockchain contract may be retrieved. For another example, data may be added to the deployed blockchain contract. For yet another example, a financial transaction specified in the deployed blockchain contract may be executed. Notwithstanding the above, other types of blockchain systems and associated consensus rules may be applied to the disclosed blockchain system.

Figure 2:
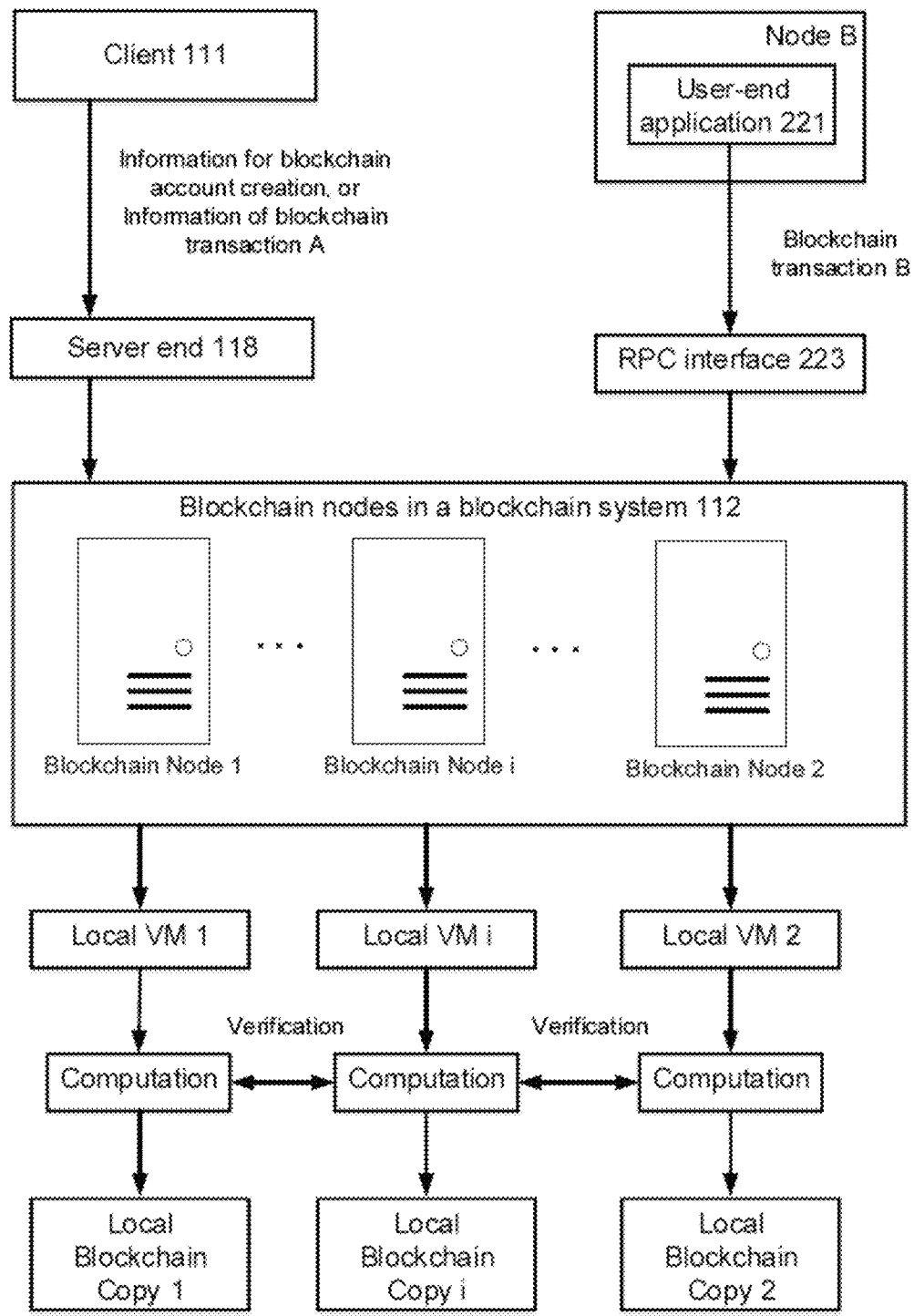
FIG. 2 illustrates a framework for implementing blockchain transactions in accordance with some embodiments.

FIG. 2 illustrates a framework for implementing blockchain transactions in accordance with some embodiments. In some embodiments, the client 111 may transmit information (e.g., a request with relevant information for creating a blockchain account) to the server end 118 for the server end 118 to create a blockchain account. To this end, the server end 118 may generate cryptography keys, compile the request with other account creation requests, and/or perform other operations. Then, the server end 118 may transmit a blockchain transaction (e.g., blockchain transaction A) including the compiled account creation requests to one or more of blockchain nodes for execution.

In some embodiments, Node B may construct a signed blockchain transaction and transmit it to one or more blockchain nodes for execution. In one embodiment, Node B may construct a blockchain transaction B. The blockchain transaction B may comprise a blockchain contract B for deployment or invoking a deployed blockchain contract. For example, the blockchain transaction B may comprise a blockchain contract that creates a blockchain account or invokes a deployed blockchain contract A. The blockchain contract B may be programmed in source code at a user-end application 221. For example, a user or machine may program the blockchain contract B. Node B may compile the source code using a corresponding compiler, which converts the source code into bytecode. The blockchain transaction B may comprise information such as nonce (e.g., transaction serial number), from (e.g., a blockchain address of Node B or another blockchain address), to (e.g., empty if deploying a blockchain contract), transaction fee, value (e.g., transaction amount), signature (e.g., signature of Node B), data (e.g., message to a contract account), etc. The Node B may send the blockchain transaction B to one or more blockchain nodes through a remote procedure call (RPC) interface 223 for execution. RPC is a protocol that a first program (e.g., user-end application) can use to request a service from a second program located in another computer on a network (e.g., blockchain node) without having to understand the network's details. When the first program causes a procedure to execute in a different address space, it is as if a normal (local) procedure call, without the programmer explicitly coding the details for the remote interaction.

In some embodiments, on receiving the blockchain transaction (e.g., blockchain transaction A or B), the recipient blockchain may verify if the blockchain transaction is valid. For example, the signature and other formats may be verified. If the verification succeeds, the recipient blockchain node may broadcast the received blockchain transaction (e.g., blockchain transaction A or B) to the blockchain network including various other blockchain nodes. Some blockchain nodes may participate in the mining process of the blockchain transactions. The blockchain transaction may be picked by a certain node for consensus verification to pack into a new block. If the blockchain transaction involves a blockchain contract, the certain node may create a contract account for a blockchain contract in association with a contract account address. If the blockchain transaction involves invoking a deployed blockchain contract, the certain node may trigger its local VM to execute the received blockchain transaction, thereby invoking the deployed blockchain contract from its local copy of the blockchain and updating the account states in the blockchain. If the certain node succeeds in mining a new block, the certain node may broadcast the new block to other blockchain nodes. The other blockchain nodes may verify the new block as mined by the certain blockchain node. If consensus is reached, the blockchain transaction B is respectively packed to the local copies of the blockchain maintained by the blockchain nodes. The blockchain nodes may similarly trigger their local VMs to execute the blockchain transaction B, thus invoking the blockchain contract A deployed on the local copies of the blockchain and making corresponding updates.

Upon receiving the new block, the other blockchain nodes may perform verifications. If a consensus is reached that the new block is valid, the new block is respectively packed to the local copies of the blockchain maintained by the blockchain nodes. The blockchain nodes may similarly trigger their local VMs (e.g., local VM 1, local VM i, local VM 2) to execute the blockchain transactions in the new block, thus invoking local copies of the blockchain (e.g., local blockchain copy 1, local blockchain copy i, local blockchain copy 2) and making corresponding updates. The hardware machine of each blockchain node may have access to one or more virtual machines, which may be a part of or couple to the corresponding blockchain node. Each time, a corresponding local VM may be triggered to execute the blockchain transaction. Likewise, all other blockchain transactions in the new block will be executed. Lightweight nodes may also synchronize to the updated blockchain.

Figure 3:
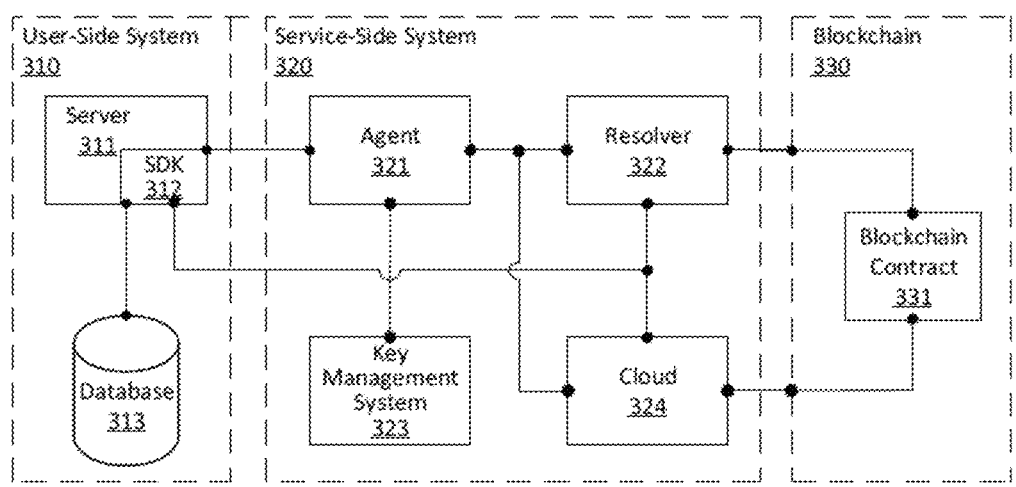
FIG. 3 illustrates a network environment associated with a system for managing decentralized identifiers and verifiable claims in accordance with some embodiments.

FIG. 3 illustrates a network environment associated with a system for managing decentralized identifiers and verifiable claims in accordance with some embodiments. In some embodiments, a user-side system 310 may correspond to an entity. The entity may be a business entity that provides one or more products or services to a plurality of users. The entity may also be an individual user, a group of users, an organization, other suitable entities, or any combination thereof. The use-side system 310 may comprise a plurality of computer systems, data stores, cloud services, mobile applications, other suitable components, or any combination thereof. The user-side system 310 may comprise a server 311 and a database 313. The database 313 may store data associated with a plurality of user accounts of the users of the entity. The entity corresponding to the user-side system 310 may desire to create and manage DIDs and VCs for itself as well as its users. It may comprise one or more software development kits (SDKs) 312 for managing creation and authentication of DIDs or issuance and verification of VCs.

In some embodiments, to implement functionalities associated with DIDs and VCs, the user-side system 310 may interface with a service-side system 320. In some embodiments, the service-side system 320 as illustrated in FIG. 3 may be equivalent to, be part of, or comprise one or more components of the server end 118 as illustrated in FIGS. 1 and 2. The service-side system 320 may comprise one or more agents 321, one or more resolvers 322, one or more key management systems 323, one or more clouds 324, other suitable components or any combination thereof. The agent 321 may provide various services or applications related to DIDs or VCs and maintain databases mapping account information or other business data from the user-side system 310 to DIDs, VCs, or other information or data stored on one or more blockchains. The agent 321 may provide one or more application programming interfaces (APIs), which may be used by the user-side system 310 to directly submit requests related to DIDs or VCs. The agent 321 may manage communications between the user-side system 310 and the resolver 322 and the cloud 324.

In some embodiments, the agent 321 may be coupled to a key management system (KMS) 323. The KMS 323 may generate, distribute, and manage cryptographic keys for devices and applications. It may cover security aspects from secure generation of keys over the secure exchange of keys to secure key handling and storage. The functionalities of the KMS 323 may include key generation, distribution, and replacement as well as key injection, storing, and management. The KMS 323 may comprise or be coupled to a trusted execution environment (TEE). The TEE may be an isolated area on the main processor of a device that is separate from the main operating system. The TEE may provide an isolated execution environment offering security features such as isolated execution, integrity of applications executing with the TEE, along with confidentiality of their assets. It may guarantee code and data loaded inside to be protected with respect to confidentiality and integrity. In some embodiments, the KMS 323 may generate one or more cryptographic key pairs in the TEE. Before outputting the cryptographic key pair, the TEE may encrypt the private key. The encryption of the private key can be based on various methods or standards, such as Data Encryption Standard (DES), TripleDES, RSA, Advanced Encryption Standard (AES), Twofish, etc. The KMS 323 may store the encrypted private key in association with the public key. To use the private key, the KMS 323 may feed the encrypted private key to the TEE for decryption and processing.

In some embodiments, the agent 321 may be coupled to a resolver 322, which may comprise software applications for managing interactions between the agent and a blockchain 330 in transactions related to DIDs or VCs (e.g., correspondence between a DID and a DID document). Herein, depending on the context, the blockchain 330 may refer to a ledger of records or a blockchain system that comprises a decentralized network of nodes that store the ledger of records and participate in a consensus process for adding data to the ledger of records. The resolver 322 may be part of or coupled to the one or more cloud-based services. The one or more cloud-based services may be associated with a blockchain-as-a-service (BaaS) cloud 324 or other suitable cloud services. The BaaS cloud 324 may constitute a platform that offers various interfaces to one or more blockchains 330. It may receive inputs from an external application and facilitate the creation and execution of operations such as blockchain transaction deployment, blockchain contract creation and execution, blockchain account creation based on the inputs. The BaaS cloud 324 may also obtain information and data from one or more blockchains 330 and feed the information and data to one or more other systems using the BaaS cloud 324. In some embodiments, the agent 321 may be directly coupled to the cloud 324 to use its services. In some embodiments, one or more of the agent 321, the resolver 322, and the KMS 323 may be integrated as part of the BaaS cloud 324 or another suitable online platform.

In some embodiments, the resolver 322 and cloud 324 may be coupled to a blockchain 330. The blockchain 330 may comprise one or more blockchain contracts 331. One or more of the blockchain contracts 331 may be configured to be executed by a virtual machine associated with the blockchain 300 to perform one or more operations associated with DIDs and VCs. The operations may comprise creating a new DID, storing a DID document, updating a DID document, identifying a DID document based on a DID, storing information associated with a VC, retrieving information associated with a VC, other suitable operations, or any combination thereof. The resolver 322 and cloud 324 may be configured to deploy one or more transactions on the blockchain 330 that invoke one or more of the blockchain contracts 331. The transactions may trigger one or more operations related to DIDs and VCs.

Figure 4:
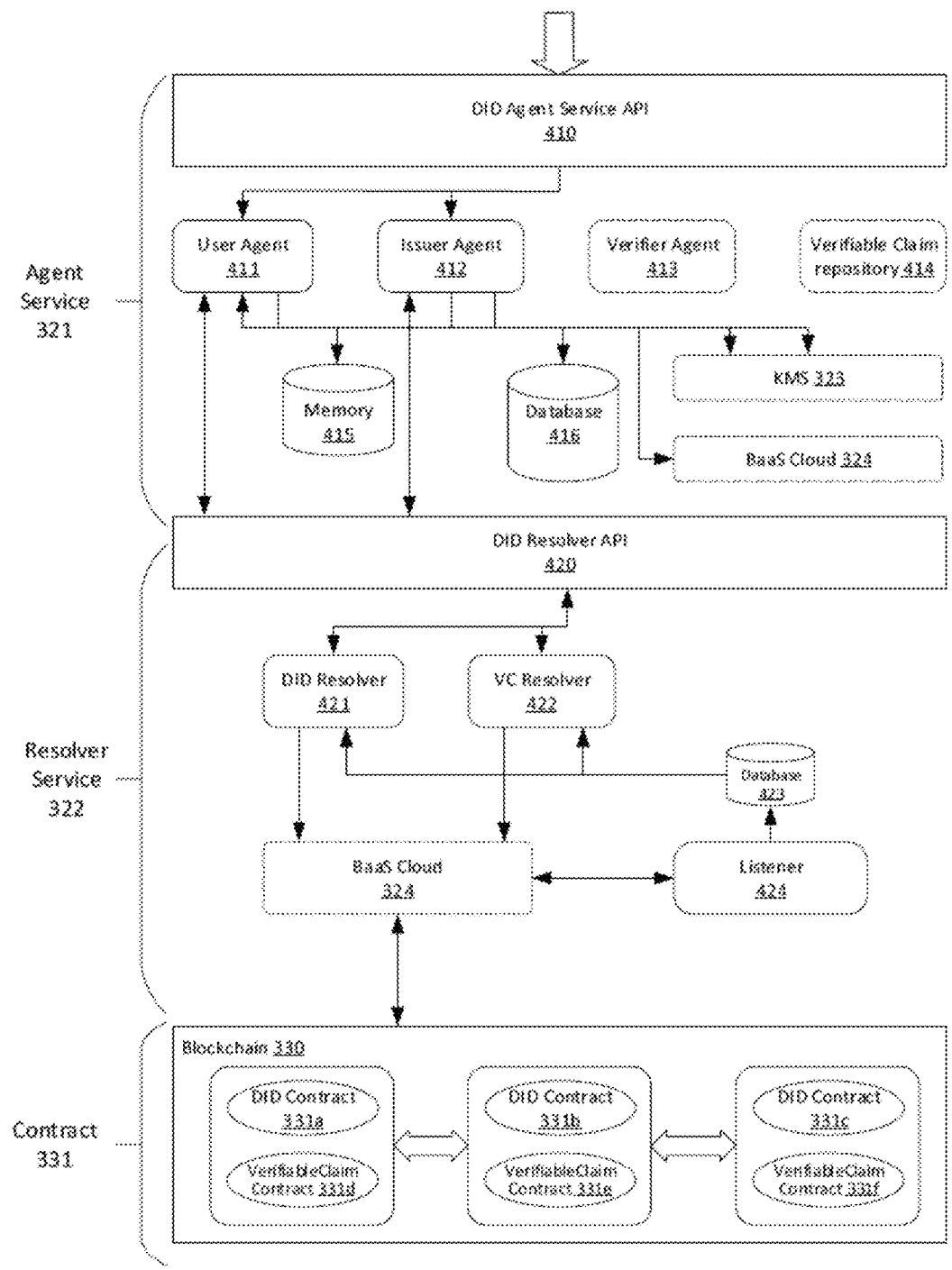
FIG. 4 illustrates an architecture associated with a blockchain-based system for managing decentralized identifiers and verifiable claims in accordance with some embodiments.

FIG. 4 illustrates an architecture associated with a blockchain-based system for managing decentralized identifiers and verifiable claims in accordance with some embodiments. In some embodiments, the system may comprise three main components, one or more agent services 321, one or more resolver services 322, and one or more blockchain contracts 331. The one or more agent services 321 may be configured to process requests related to DIDs and VCs that are received from users. The one or more agent services 321 may manage mapping relationships between account information on user-side systems 310 and DIDs of the owners of the accounts. The agent services 321 may comprise a DID agent service API 410 for receiving DID-related requests from user-side systems 310. Depending on the nature of a request, it may be fed to a user agent 411 for performing operations such as creation and authentication of DIDs or an issue agent 412 for performing operations such as issuance of VCs. The requests from a party desiring to verify a VC may be fed to the verifier agent 413. The one or more agent services 321 may also provide a verifiable claim repository 414 for storing one or more VCs. The agent services 321 may also use one or more memories 415 and one or more databases 416. The agent services 321 may be coupled to a KMS 323 and a BaaS Cloud 324. The agent services 321 may be coupled to the resolver services 322.

In some embodiments, one or more agents of the agent services 321 may send one or more requests to a DID resolver API 420 associated with the resolver services 322. The resolver services 322 may be configured to process interactions between the agent services 321 and the blockchain 330. The resolver services 322 may perform operations such as obtaining data from the blockchain 300, adding data to the blockchain 330, creating blockchain contracts 331, deploying transaction to the blockchain 330 to invoke blockchain contracts 331, other suitable operations, or any combination thereof. The resolver services 322 may comprise a DID resolver 421 configured to manage DIDs and DID documents stored on the blockchain 330 and a VC resolver 422 configured to manage VCs for DIDs created based on the blockchain 330. The resolver services 322 may also comprise a listener 424 for obtaining data from the blockchain 331. The listener 424 may store obtained data to a database 423. The data may be used by the DID resolver 421 and the VC resolver 422. The DID resolver 421, VC resolver 422, and listener 424 may be coupled to a BaaS cloud 324 for interactions with the blockchain 330.

In some embodiments, the blockchain 330 may comprise one or more blockchain contracts (331*a*, 331*b*, 331*c*) for managing DIDs and DID documents and comprise one or more contracts (331*d*, 331*e*, 331*f*) for managing VCs. The contracts may be executed by one or more virtual machines associated with the blockchain 330 to perform operations such as creating DIDs, storing DID documents, updating DID documents, storing information associated with VCs, other suitable operations, or any combination thereof.

Figure 5:
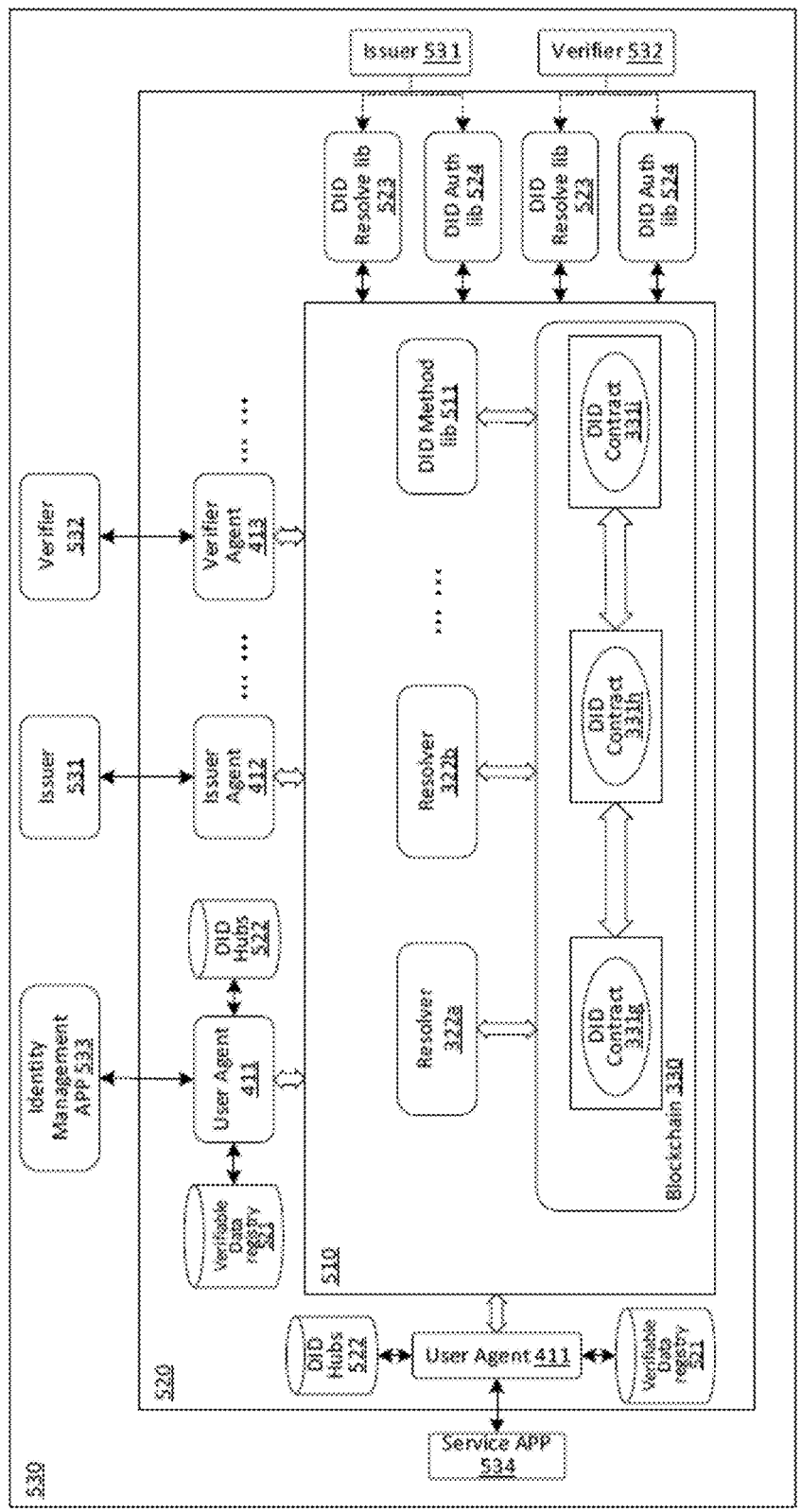
FIG. 5 illustrates a network environment associated with a system for implementing various examples of functionalities associated with decentralized identifiers and verifiable claims in accordance with some embodiments.

FIG. 5 illustrates a network environment associated with a system for implementing various examples of functionalities associated with decentralized identifiers and verifiable claims in accordance with some embodiments. Components of the network environment may be categorized into three layers 510, 520, and 530. In some embodiments, the bottom or core layer 510 may comprise one or more blockchains 330, which may comprise one or more blockchain contracts (331*g*, 331*h*, 331*i*) that can be executed to perform operations related to DIDs and VCs. The blockchain 330 may store a plurality of DIDs and a plurality of DID documents corresponding to the DIDs. The blockchain contracts (331*g*, 331*h*, 331*i*) may be configured to manage mapping relationships between DIDs and DID documents, as well as creation and changes to DID documents. The blockchains 330 may be accessible to one or more resolvers (322*a*, 322*b*) for operations related to DIDs and VCs. The resolvers (322*a*, 322*b*) may be configured to provide to an external system services such as searching for DID documents or data contained in DID documents based on inputted DIDs. One or more method libraries 511 may also be available for external systems to adopt to interact with the blockchain 330.

In some embodiments, the middle or enhancement layer 520 may comprise one or more user agents 411, one or more issuer agents 412, or one or more verifier agents 413. In some embodiments, the blockchain 330 may comprise a consortium blockchain, which may or may not be directly accessible to users that are not consensus nodes of the consortium blockchain. A user agent 411 may provide an interface for an ordinary user to interact with the blockchain. In some embodiments, the user agent 411 may be configured to create one or more DIDs, authenticate one or more DIDs, interact with one or more verifiable data registry 521 or one or more DID hubs 522, send notifications to an owner of a DID, perform other suitable functionalities, or any combination thereof. Here, a DID hub 522 may comprise a system in which an owner of a DID stores its sensitive data. The owner may grant certain other entities (e.g., institutions issuing verifiable claims) access to data stored in the DID hub 522. A verifiable data registry 521 may comprise a VC repository for storing and managing the VCs issued to an owner of a DID. An issuer agent 412 may comprise one or more APIs (e.g., REST API) or SDKs. The issuer agent 412 may be configured to issue one or more verifiable claims, withdraw one or more verifiable claims, check and inspect an existing verifiable claim, publish a template for verifiable claims, maintain a template for verifiable claims, perform other suitable operations, or any combination thereof. A verifier agent 413 may comprise one or more APIs (e.g., REST API) or SDKs and be configured to verify a verifiable claim or perform one or more other suitable operations. In some embodiments, the layer 520 may also comprise one or more code libraries (e.g., DID resolve library 523, DID authentication library 524) that can be adopted and used to interact with the DID resolvers 322 or directly with the blockchain 330. The code libraries may be packaged into one or more SDKs and be used to perform functionalities such as DID authentication, interactions with the blockchain 300, or interfacing with blockchain contracts 331. The issuer agent 412 and verifier agent 413 may be used by key participants in the network environment associated with DIDs and VCs such as entities able to perform know-your-customer (KYC) authentication or endorsement for users or to issue or verify verifiable claims (e.g., government institutions, banks, financial service providers). The key participants may provide third-party services that can be integrated via connections with the issuer agent 412, the verifiable agent 413, or other suitable components of the network environment.

In some embodiments, the upper or extension layer 530 may comprise one or more external services or applications related to DIDs and VCs. The services or applications may comprise one or more issuer applications 531, one or more verifier applications 532, an identity management application 533, a service application 534, one or more other suitable services or applications, or any combination thereof. An issuer application 531 may correspond to an entity (e.g., government institution, banks, credit agency) issuing verifiable claims signed or endorsed by the entity for users. The issuer application 531 may operate on a user-side system 310. The issuer application 531 may comprise an issuer verifiable claim manager service which may allow an issuer to manage issued VCs, maintain their status (e.g., validity), or perform other suitable operations. The issuer application 531 may interact with the layers 510 and 520 via a connection or interface with the issuer agent 412 or one or more code libraries 523 and 524. A verifier application 532 may correspond to an entity (e.g., service provider, credit issuer) needing to verify verifiable claims to ascertain a user's information (e.g., identity, age, credit score). The verifier application 532 may operate on a user-side system 310. The verifier application 532 may interact with layers 510 and 520 via a connection or interface with the verifier agent 413 or one or more code libraries 523 and 524. The identity management application 533 may be installed on a client device or terminal associated with a user. The user may be a DID owner, which may be an individual, a business, an organization, an application, or any other suitable entity. The identity management application 533 may allow a user to manage cryptographic key pairs associated with DIDs, original data, or VCs, to receive notifications from a user agent 411, to authenticate a DID, to grant access to data, to use a VC, to perform other suitable operations, or any combination thereof. The identity management application 533 may interact with the layers 510 and 520 via a connection or interface with the user agent 411. The service application 534 may also be coupled to the user agent 411 and be configured to manage functions related to DIDs or VCs for one or more users or accounts.

FIGS. 6-10 illustrate example operations associated with DIDs or VCs performed by one or more user-side systems 310, one or more resolvers 322, one or more clouds 324, or one or more blockchain systems 330. In some embodiments, a user-side system 310 may manage one or more DIDs or one or more VCs by interfacing with a DID resolver 322 and a blockchain 330 storing DIDs and DID documents. The user-side system 310 may use one or more SDKs 312 for managing DIDs that are compatible with methods associated with the DIDs. The SDKs 312 may be integrated with one or more applications used by the user-side system 310. The user-side system 310 may also interface with one or more service endpoints for storing verifiable claims, one or more service endpoints for storing status information for verifiable claims, one or more service endpoints for authentication of DIDs, other suitable systems, or any combination thereof.

Figure 6:
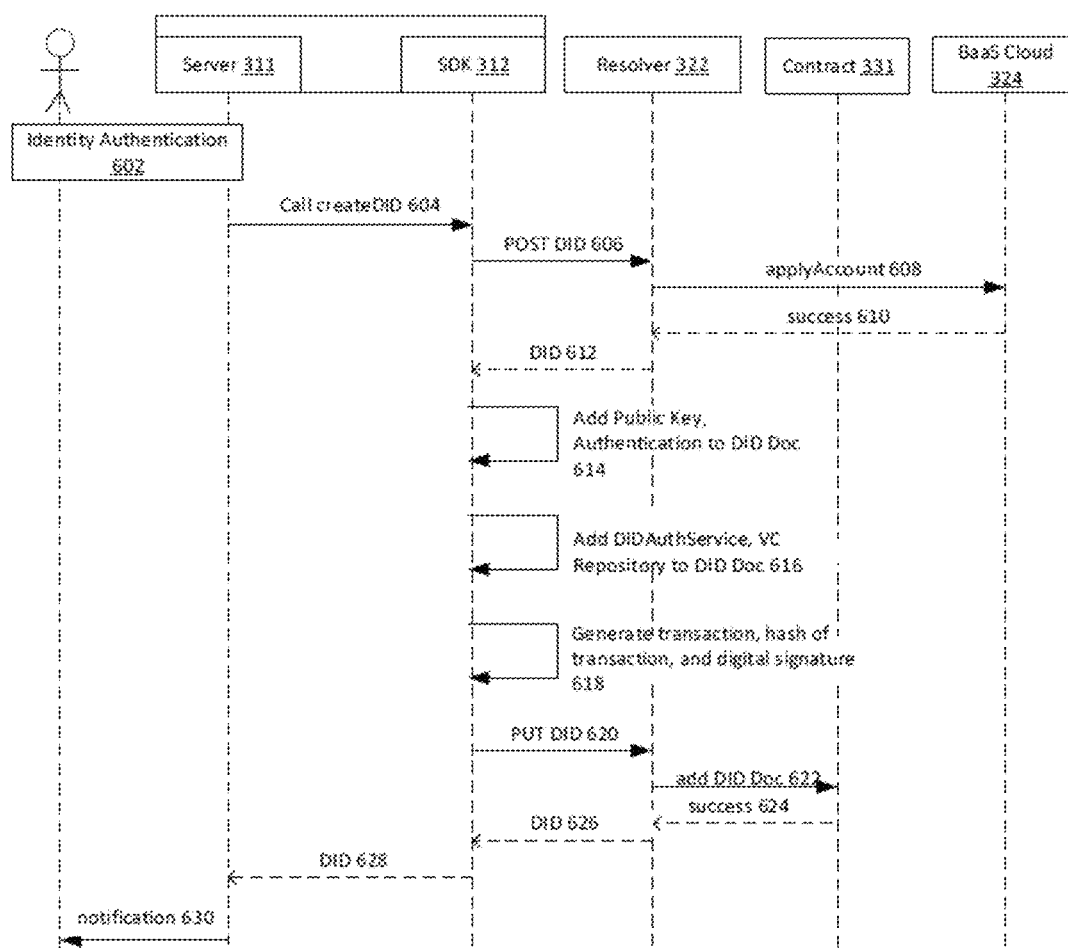
FIG. 6 illustrates a method for creating a decentralized identifier in accordance with some embodiments.

FIG. 6 illustrates a method for creating a decentralized identifier in accordance with some embodiments. The operations of the method presented below are intended to be illustrative. Depending on the implementation, the method may include additional, fewer, or alternative steps performed in various orders or in parallel. The method may start at step 602, in which a server 311 of a user-side system 310 may obtain identity authentication for a user for whom it is going to obtain a DID. The user-side system 310 may also generate or retrieve a cryptographic key pair including a public key and a private key for use to create the DID. At step 604, the server may invoke a functionality of an SDK 312 for creating a new DID. Here, at least a public key of the cryptographic key pair may be inputted or otherwise made available to the SDK 312. At step 606, the user-side system 310 may send a request for creating a new DID to the resolver 322 using the SDK 312. At step 608, the resolver 322 may send a request to a blockchain system 330 for creating a new blockchain account. Here, the request may be directly sent to one or more blockchain nodes of the blockchain 330 in the form of one or more blockchain transactions or be sent to a BaaS Cloud 324 or other suitable interface systems associated with a blockchain 330. In response to the request from the resolver 322, at step 610, the resolver 322 may obtain an indication that a new blockchain account has been created from the cloud 324. The blockchain account may be associated with an address on the blockchain 330. The information obtained by the resolver 322 may comprise information associated with the newly-created blockchain address. It may comprise a newly-created DID or at least information sufficient to construct the DID. At step 612, the resolver 322 may send a message back to the SDK 312 associated with the user-side system 310. The message may comprise information associated with the newly created DID.

In some embodiments, a DID document may be created and stored on the blockchain 330. At step 614, the user-side system may use the SDK 312 to generate a DID document and add the public key associated with the newly-created DID and authentication information to the DID document. At step 616, the user-side system 310 may use the SDK 312 to add information associated with one or more service endpoints (e.g., information associated with an authentication service endpoint, information associated with a verifiable claim repository) to the DID document. The authentication service endpoint and the verifiable claim repository may be provided as part of a system including the resolver 322 or be provided by third-party systems. Then, at step 618, the user-side system may use the SDK 312 to generate one or more blockchain transactions for storing the DID document to the blockchain 330. The user-side system 310 may also use the SDK 312 to generate a hash value of the blockchain transaction and generate a digital signature for the transaction using the private key associated with the DID. At step 620, the SDK 312 may send the DID document as well as the blockchain transaction to the DID resolver 322 for sending to the blockchain system. At step 622, the DID resolver may send one or more transactions to the blockchain system (e.g., one or more blockchain nodes, a BaaS Cloud 324). The one or more transactions may invoke a blockchain contract 331 for managing DIDs and DID documents on the blockchain 330. At step 624, the resolver 322 may obtain information from the blockchain 330 indicating that the DID document has been successfully stored. At step 626, the resolver 322 may forward a confirmation to the SDK 312. At step 628, the SDK 312 may send information associated with the created DID and DID document to the server 311 of the user-side system 310, which may then send a notification to the user confirming successful creation of the DID at step 630.

Figure 7:
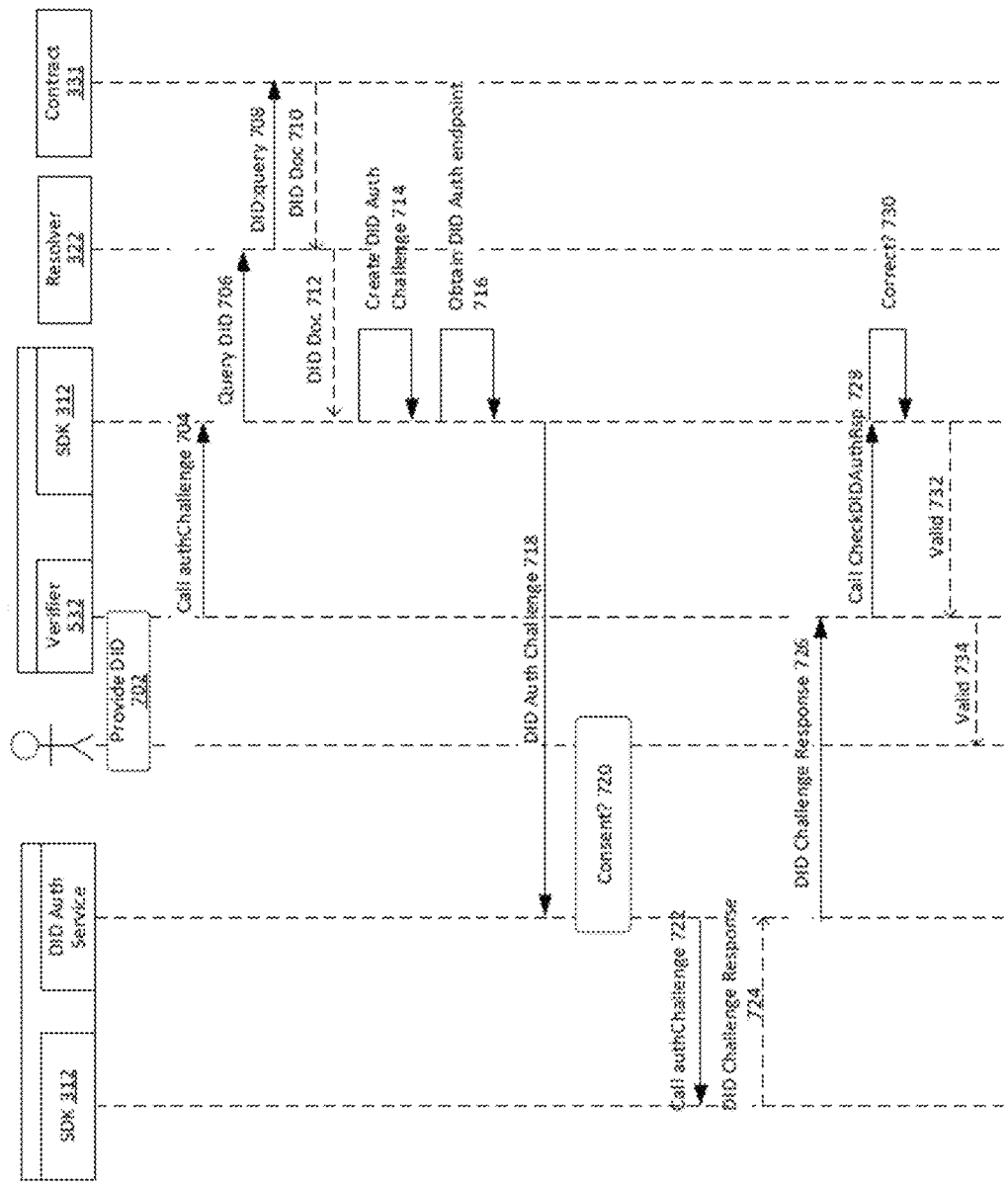
FIG. 7 illustrates a method for authenticating a decentralized identifier using DID authentication services in accordance with some embodiments.

FIG. 7 illustrates a method for authenticating a decentralized identifier using DID authentication services in accordance with some embodiments. The operations of the method presented below are intended to be illustrative. Depending on the implementation, the method may include additional, fewer, or alternative steps performed in various orders or in parallel. In some embodiments, a user owning a DID may use DID authentication services provided by a business entity to achieve authentication of its ownership of the DID. The owner may trust a public-private key pair corresponding to the DID to the business entity for storage. The owner may provide a network location (e.g., identified by a URL) of the DID authentication services as a service endpoint for authentication of the DID. The location identifier of the DID authentication services may be included in a "service" filed of the DID document associated with the DID.

In some embodiments, a verifier 532 (e.g., a service provider needing to verify information of a customer) may initiate a DID authentication process using an SDK 312. At step 702, the verifier 532 may obtain the DID provided by a purported owner. At step 704, the verifier 532 may call the SDK 312 to create a DID authentication challenge. The verifier 532 may input to the SDK 312 the DID to be authenticated and a network address (e.g., a URL) to which a response to the challenge is to be sent. At step 706, the SDK 312 may send a query to a resolver 322 for the DID document associated with the DID to be authenticated. At step 708, the resolver 322 may formulate a blockchain transaction invoking a blockchain contract 331 for managing DIDs and send the blockchain transaction to one or more blockchain nodes associated with the blockchain 330 for execution. As a result, the resolver 322 may obtain the DID document corresponding to the DID at step 710 and forward it to the SDK 312 at step 712. At step 714, the verifier 532 may use the SDK 312 to create a DID authentication challenge based on the obtained DID document. In some embodiments, the DID authentication challenge may comprise a ciphertext created by encrypting original text using a public key associated with the DID that is recorded in the DID document. The challenge may also comprise a network address to which a response is to be sent. At step 716, the verifier 532 may obtain information associated with the authentication service endpoint for the DID from the DID document. At step 718, the verifier 532 may use the SDK 312 to send the challenge to the DID authentication services associated with the DID.

In some embodiments, after obtaining the DID authentication challenge from the verifier 532, the DID authentication services may obtain consent from the owner for such authentication request at step 720. If the owner provides consent or permission for the identity authentication, the DID authentication services may call its version of the SDK 312 to create a response to the DID authentication challenge at step 722. In some embodiments, the response to the DID authentication challenge may comprise plaintext that is the result of decrypting the ciphertext in the challenge using the private key associated with the DID. The SDK 312 may return the response to the DID authentication services at step 724, which may then send the response to the network address provided by the verifier 432 at step 726. Upon receiving the response to the DID authentication challenge, the verifier 532 may call its SDK 312 at step 728 to check the response. At step 730, the SDK 312 may determine whether the response proves that the user providing the DID is the owner of the DID. In some embodiments, the SDK 312 may check the response by comparing decrypted text in the response with the original text that was used to create the DID authentication challenge. If the response is determined to be correct, the SDK 312 may return a message to the verifier 532 indicating the DID is a valid proof of identity of the user at step 732. At step 734, the verifier 532 may notify the user as to the validity of the DID.

Figure 8:
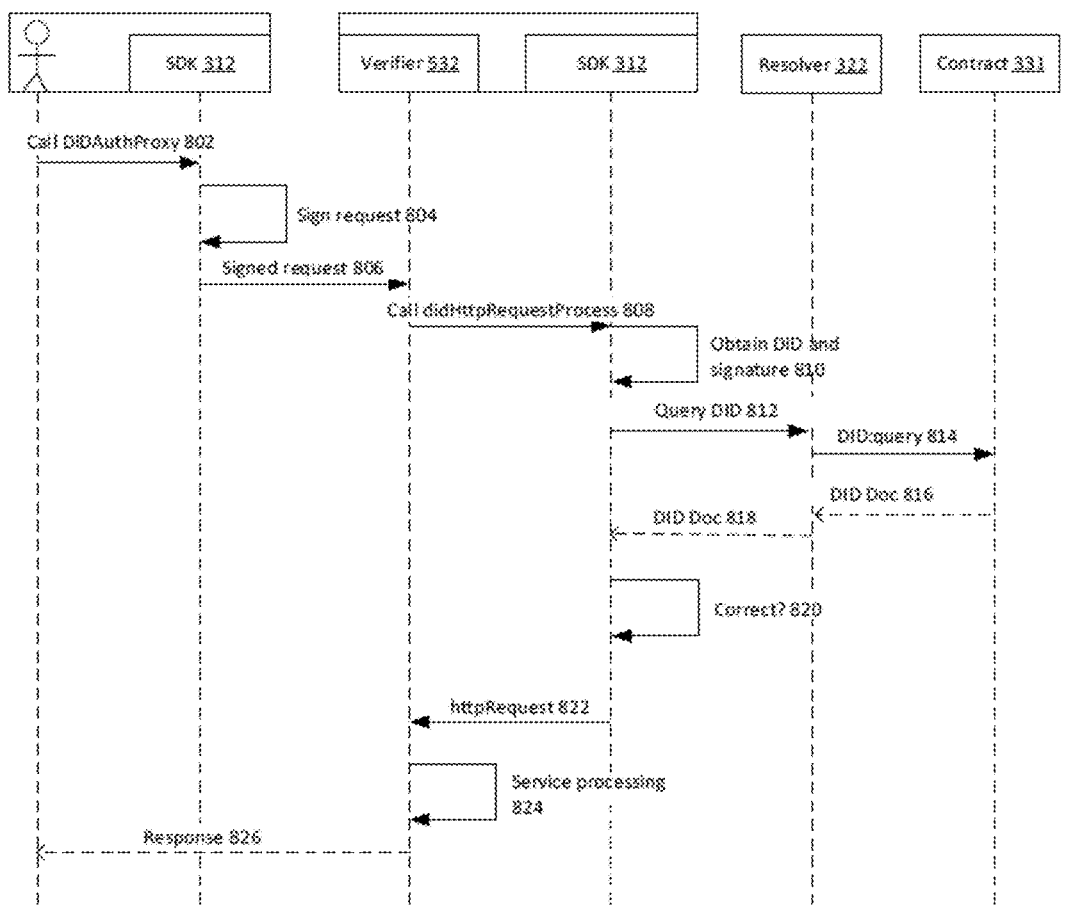
FIG. 8 illustrates a method for authenticating a decentralized identifier using an identity management application in accordance with some embodiments.

FIG. 8 illustrates a method for authenticating a decentralized identifier using an identity management application in accordance with some embodiments. The operations of the method presented below are intended to be illustrative. Depending on the implementation, the method may include additional, fewer, or alternative steps performed in various orders or in parallel. In some embodiments, a user may use a terminal for managing DIDs, which may comprise an identity management application or another suitable application. The application may comprise a version of the SDK 312. In this example, the user may need services from a service provider (i.e., verifier), which requires verification that the user owns a particular DID in order to provide its services. The user may send a service request to the verifier. The service request may be in the form of an HTTP request.

At step 802, the user may call the identity management application to provide authentication information for the service request. The user may provide the original service request as an input to the SDK 312 included in the identity management application. At step 804, the SDK 312 may sign the content of the original service request using a private key of a cryptographic key pair associated with the DID. The SDK 312 may be used to add the DID and a digital signature for the original service request to the original service request to create a signed service request. In case the original service request is a HTTP request, the SDK 312 may add the DID and the digital signature to a header of the HTTP request. At step 806, the SDK 312 may send the signed service request to the verifier 532.

In some embodiments, the verifier 532 may call its version of an SDK 312 to authenticate the DID included in the signed service request at step 808. At step 810, the SDK 312 may obtain the DID and the digital signature included in the signed service request. In case the signed service request is an HTTP request, the DID and the digital signature may be obtained from the header of the HTTP request. At step 812, the SDK 312 may send a query to a resolver 322 for the DID document associated with the DID to be authenticated. At step 814, the resolver 322 may formulate a transaction invoking a blockchain contract 331 for managing DIDs and send the transaction to one or more blockchain nodes associated with the blockchain 330 for execution. As a result, the resolver 322 may obtain the DID document corresponding to the DID at step 816 and forward it to the SDK 312 at step 818. At step 820, the SDK 312 associated with the verifier 532 may check the signed service request to determine whether it is from the owner of the DID based on the obtained DID document. In some embodiments, the SDK 312 may sign the content of the service request using a public key obtained from DID document, and check the resulting signature against the digital signature included in the signed service request to determine if the public key is associated with the key used to create the digital signature in the signed service request. If so, the SDK 312 may determine that the service request from the user is valid. It may then send it to the verifier 532 for processing at step 822. The verifier 532 may process the service request and provide appropriate services to the user at step 824. Then, the verifier 532 may send a response to the user at step 826 to confirm completion of the requested services.

Figure 9:
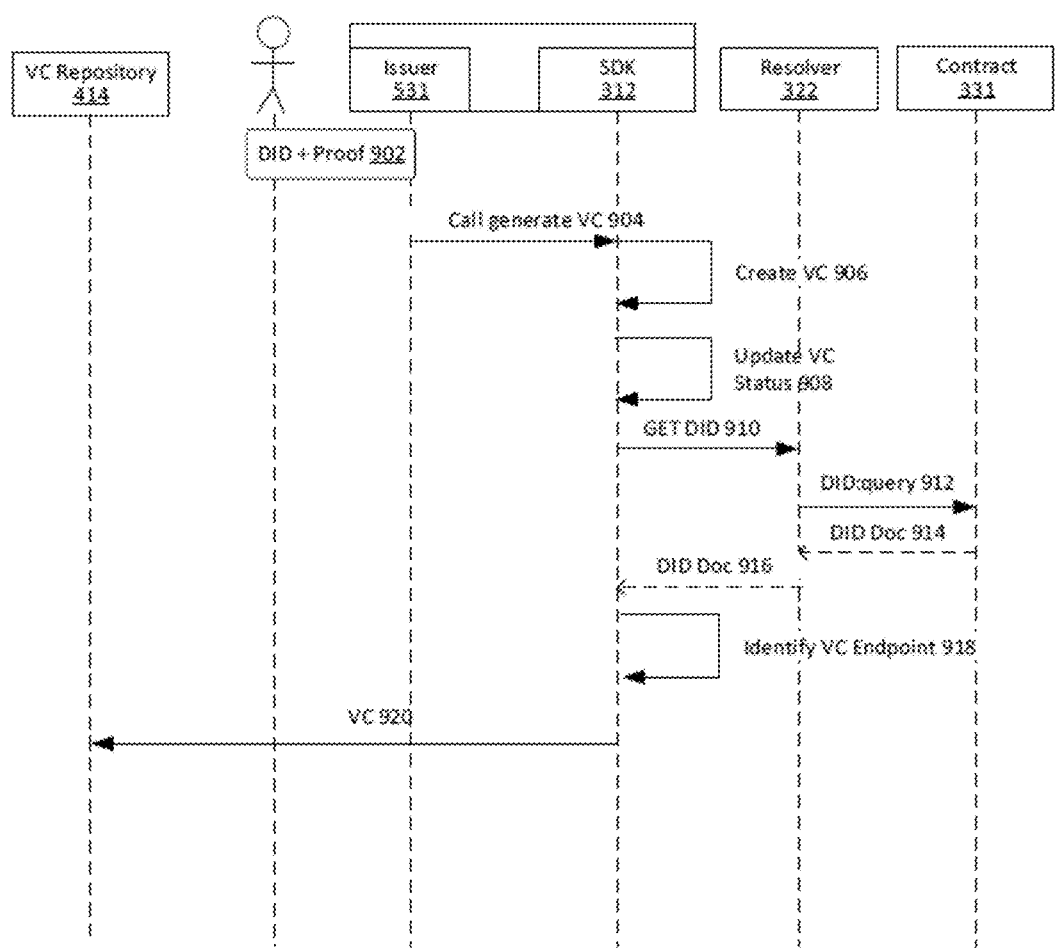
FIG. 9 illustrates a method for issuing a verifiable claim in accordance with some embodiments.

FIG. 9 illustrates a method for issuing a verifiable claim in accordance with some embodiments. The operations of the method presented below are intended to be illustrative. Depending on the implementation, the method may include additional, fewer, or alternative steps performed in various orders or in parallel. In some embodiments, an issuer 531 may issue a VC to a user. The VC may be used as a proof of certain facts or characteristics of the user as endorsed by the issuer 531.

At step 902, the issuer 531 may obtain a DID associated with the user and a proof of the fact to be included in the VC. Here, the proof of the fact to be included in the VC may be based on materials submitted by the user to the issuer 531, information or data obtained by the issuer 531 from third-party systems, in-person verification of the facts, other suitable sources of proof, or any combination thereof. After obtaining the DID and the proof, the issuer 531 may call an SDK 312 associated with creation of VCs to initiate a process for creating the VC at step 904. The message from the issuer 531 may comprise a statement of the proven fact or a claim about the user. The SDK 312 may create a VC document including the statement using a cryptographic key pair associated with the issuer 531. In some embodiments, the VC may include a digital signature created based on a private key associated with the issuer 531. At step 908, the SDK 312 may update a locally-stored status of the VC.

At step 910, the SDK 312 may send a query to a resolver 322 for the DID document associated with the DID for which the VC is issued. At step 912, the resolver 322 may formulate a transaction invoking a blockchain contract 331 for managing DIDs and send the transaction to one or more blockchain nodes associated with the blockchain 330 for execution. As a result, the resolver 322 may obtain the DID document corresponding to the DID at step 914 and forward it to the SDK 312 at step 916. At step 918, the SDK 312 may identify a VC service endpoint associated with the DID of the user for storing VCs. The VC service endpoint may correspond to a VC repository 414 used by the user or the owner of the DID. Then at step 920, the issuer may use the SDK 312 to send the VC to the VC repository 414 for storage. The VC may also include information associated with a VC status service endpoint, which may store and provide status information for the VC. In some embodiments, the information may comprise a network address (e.g., URL) for an issue agent service used by the issuer 531 to keep status of VCs. The VC status service endpoint may or may not be associated with the VC repository 414. The SDK 312 may provide the current status of the newly generated VC to the VC status service endpoint for storing. The status of the VC may be stored on a blockchain.

Figure 10:
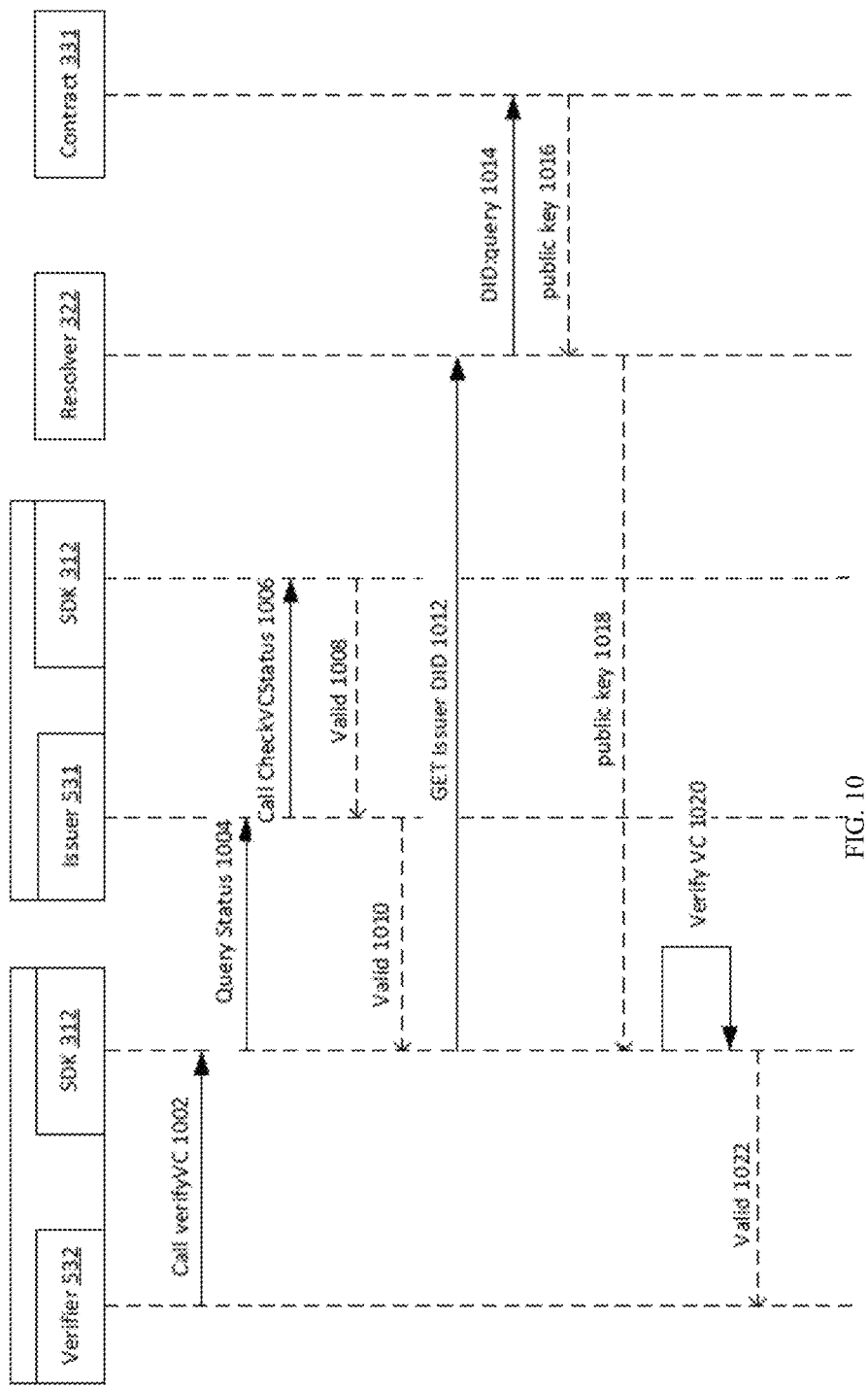
FIG. 10 illustrates a method for verifying a verifiable claim in accordance with some embodiments.

FIG. 10 illustrates a method for verifying a verifiable claim in accordance with some embodiments. The operations of the method presented below are intended to be illustrative. Depending on the implementation, the method may include additional, fewer, or alternative steps performed in various orders or in parallel. In some embodiments, a user may provide a VC to another party (e.g., a verifier 532) to prove a fact stated in the VC. The VC may be provided after the verifier 532 has verified that the user is the owner of a DID associated with the VC.

At step 1002, the verifier 532 may call an SDK 312 comprising code libraries associated with VC verification to verify the VC. The SDK 312 may identify from the VC (e.g., in a "credential status" field) information associated with a VC status service endpoint for the VC. The VC status service endpoint may be associated with an issuer 531. At step 1004, the SDK 312 may send a query to the issuer 531 for the status of the VC. In response, at step 1006, the issuer 531 may call an SDK 312 to obtain the status of the VC. The SDK 531 may obtain the status of the VC. As an example, the SDK 312 may determine that the VC has a valid status and may return the information to the issuer 531 at step 1008. Then, at step 1010, the issuer may return the valid status information to the SDK 312 associated with the verifier 532.

The verifier 532 may obtain an identifier associated with the issuer 531 of the VC. For example, the identifier may be a DID of the issuer 531. At step 1012, the SDK 312 may send a query to a resolver 322 for a public key associated with the DID of the issuer 531 of the VC. At step 1014, the resolver 322 may formulate a transaction invoking a blockchain contract 331 for managing DIDs and send the transaction to one or more blockchain nodes associated with the blockchain 330 for execution. As a result, the resolver 322 may obtain the public key corresponding to the DID at step 1016 and forward it to the SDK 312 associated with the verifier 532 at step 1018. At step 1020, the SDK 312 associated with the verifier 532 may verify the VC based on a digital signature included therein and the public key associated with the issuer 531 of the VC. If the VC is verified, the SDK 312 may send a confirmation to the verifier 532 at step 1022.

FIGS. 11-14 illustrate example operations associated with DIDs or VCs performed by one or more user-side systems 310, one or more agents 321, one or more resolvers 322, one or more clouds 324, one or more blockchain systems 330, one or more KMSs, or other suitable systems, applications, services. In some embodiments, a user-side system 310 may manage one or more DIDs or VCs by interacting with an online platform integrating one or more of the aforementioned components via one or more API interfaces (e.g., REST API). The user-side system 310 may trust confidential information such as cryptographic key pairs to the online platform for secure keeping.

Figure 11:
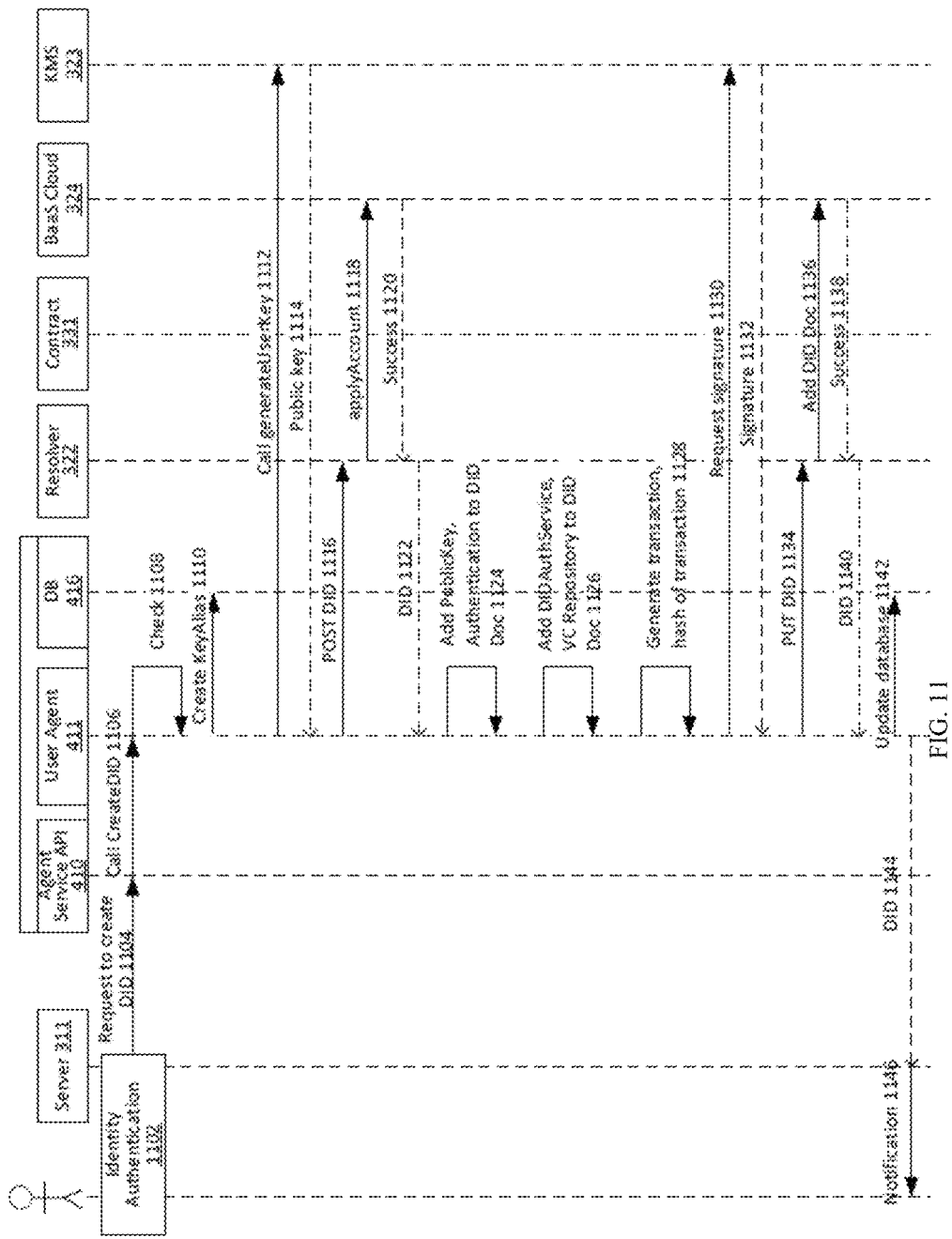
FIG. 11 illustrates a method for creating a decentralized identifier using an agent service in accordance with some embodiments.

FIG. 11 illustrates a method for creating a decentralized identifier using an agent service in accordance with some embodiments. The operations of the method presented below are intended to be illustrative. Depending on the implementation, the method may include additional, fewer, or alternative steps performed in various orders or in parallel. In some embodiments, a user-side system 310 associated with an entity may use one or more agent services 321 to create one or more DIDs for one or more users of the entity and correlate the DIDs with internal accounts or identifications (e.g., service IDs) maintained by the entity. In order to create DIDs for its users, the entity may have been authenticated by the online platform as a trusted entity and may have made a commitment to provide truthful information. In some embodiments, the entity may have been issued a VC by a bootstrap issuer DID to certify that it is authenticated by an authoritative entity. The entity may be required to authenticate the identities of its users. The user-side system 310 may use one or more KMSs 323 and the secure environment (e.g., TEE) that they provide to manage cryptographic keys associated with the created DIDs and to map the cryptographic keys to the internal accounts or identifications maintained by the entity. With the help of the agent services 321, the user-side system 310 may use services associated with DIDs without keeping a record of the DIDs. Instead, it may simply provide its internal account information or identification information for identification of the DIDs via one or more interfaces associated with the agent services 321.

In some embodiments, an online platform for managing DIDs may receive a request for creating a DID. The request may be from a first entity on behalf of a second entity for creating the DID for the second entity. In the example illustrated by FIG. 11, an entity (e.g., first entity) may create a DID for a user (e.g., second entity), who may have an account with the business entity. In some embodiments, the entity may authenticate the identity of a user before creating a DID for the user. For example, at step 1102 of FIG. 11, a server 311 of a user-side system 310 associated with the entity may perform identity authentication or otherwise obtain identity authentication information for the user. The entity may have authenticated the identity of the user earlier and may maintain such information in a database. At step 1002, the server 311 may retrieve such information. Then, at step 1004, the server 311 may send the request for creating the DID to an agent service API 410 associated with a user agent 411 associated with the online platform. The request may comprise an account identifier corresponding to the user. The request may take the form of an API message. At step 1006, the agent service API 410 may send a request to a user agent 411 for creating the DID.

At step 1108, the user agent 411 may check the request for required information. In some embodiments, to create a DID for a user, the entity may be required to have an existing DID for itself. The user agent 411 may check the request to determine that the sender of the request has an existing DID and to determine the DID associated with the sender. In some embodiments, the entity may be required to provide a proof of identity authentication for the user. The proof of identity authentication may comprise a proof of real-person authentication, a proof of real-name authentication, another suitable proof of authentication, or any combination thereof. For example, a proof of real-name authentication may be based on a user's office identification (e.g., government-issued ID). An example proof may, for example, be a number created by applying a hash function (e.g., SHA-256) to a combination of an ID type, ID number, and a number of the user. Such a proof may ensure unique correspondence with a particular user while maintaining sensitive information of the user confidential. The user agent 411 may determine whether the request comprises a proof of identity authentication and, if so, accept the request. The user agent 411 may reject the request if it does not comprise the proof of identity authentication or may send a request to the entity for a proof of identity authentication. The user agent 411 may obtain the proof of identity authentication based on the received request, which may directly comprise the proof or information associated with means to obtain the proof. If the request comprises the required information, the user agent 411 may create a key alias corresponding to the proof of identity authentication for the user at step 1110.

In some embodiments, the user agent 411 may obtain, in response to receiving the request, a public key of a cryptographic key pair. The public key may later be used as a basis for creating the DID. In some embodiments, the user agent 411 may obtain the public key from the KMS 323. At step 1112, the user agent 411 may send a request to the KMS 323 for generating and storing a cryptographic key pair. The KMS 323 may generate a cryptographic key pair. In some embodiments, the KMS 323 may cause the cryptographic key pair to be generated in a TEE associated with the KMS 323. After the key pair is generated, the KMS 323 may obtain a public key and an encrypted private key from the TEE. At step 1114, the KMS 323 may send the public key to the user agent 411.

In some embodiments, the online platform may obtain the DID based on the public key. At step 1116, the user agent 411 may send a request for creating a new DID to the resolver 322 The request may comprise the public key. In response, the resolver 322 may generate, based on the public key, one or more blockchain transactions for creating the DID and adding a DID document associated with the DID to a blockchain. Alternatively, the DID resolver may send a request to the BaaS cloud 324 for generation of such transactions. For example, at step 1118, the resolver 322 may send a request to a blockchain system 330 for creating a new blockchain account. Here, the request may be directly sent to one or more blockchain nodes of the blockchain 330 in the form of one or more blockchain transactions or be sent to a BaaS Cloud 324 or other suitable interface systems associated with a blockchain 330. The blockchain transactions may invoke one or more blockchain contracts configured for managing DIDs. In response to the request from the resolver 322, at step 1120, the DID resolver may obtain an indication from the blockchain 330 or the cloud 324 that a new blockchain account is successfully created. The blockchain account may be associated with an address on the blockchain 330. Information obtained by the resolver 322 may comprise information associated with the newly-created blockchain address. It may directly comprise a newly-created DID or at least information sufficient to construct the DID. At step 1122, the resolver 322 may send a message back to the user agent 411. The message may comprise information associated with the newly created DID.

In some embodiments, a DID document may be created and stored in the blockchain 330. At step 1124, the user agent 411 may generate a DID document and add the public key associated with the newly-created DID and authentication information to the DID document. At step 1126, the user agent 411 may add information associated with one or more service endpoints (e.g., information associated with an authentication service endpoint, information associated with a verifiable claim repository) to the DID document. The authentication service endpoint and the verifiable claim repository 414 may be provided as part of the online platform. The DID document may comprise one or more public keys associated with the obtained DID, authentication information associated with the obtained DID, authorization information associated with the obtained DID, delegation information associated with the obtained DID, one or more services associated with the obtained DID, one or more service endpoints associated with the obtained DID, a DID of a creator of the obtained DID, other suitable information, or any combination thereof. In some embodiments, the DID document may comprise a "creator" field containing identification information (e.g., DID) of the entity that sent the request for creating the DID on behalf of the user. The "creator" field may serve as a record of the entity that authenticated of the identity of or endorsed the owner of the DID. Then, at step 1128, the user agent 411 may generate one or more blockchain transactions for storing the DID document to the blockchain 330. The user agent 411 may also generate one or more hash values of the blockchain transactions.

In some embodiments, for the one or more blockchain transactions to be executed by one or more nodes of the blockchain 330, they are required to be signed using the private key associated with the DID. The user agent 411 may obtain such a digital signature from the KMS 323. At step 1130, the user agent 411 may send a request to the KMS 323 for signing a blockchain transaction using the private key of the cryptographic key pair associated with the DID. The request may comprise the hash value of the transaction and a public key associated with the DID. The KMS 323 may create a digital signature for the transaction. In some embodiments, the digital signature may be generated in a TEE associated with the KMS 323. The KMS 323 may identify an encrypted private key associated with the public key and feed the encrypted private key to the TEE. The encrypted private key may be decrypted within the TEE and used to generate the digital signature for the transaction. The digital signature may then be fed back to the KMS 323. At step 1132, the user agent 411 may receive from the KMS a signed version of the blockchain transaction.

At step 1134, the user agent 411 may send the DID document as well as the signed blockchain transaction to the resolver 322 for sending to the blockchain system. At step 1136, the resolver 322 may send one or more transactions to the blockchain system (e.g., one or more blockchain nodes, a BaaS Cloud 324). The transactions may invoke a blockchain contract 331 for managing DIDs and DID documents on the blockchain 330. At step 1138, the resolver 322 may obtain information from the blockchain 330 indicating that the DID document has been successfully stored. At step 1140, the resolver 322 may forward a confirmation to user agent 411.

At step 1142, after a DID and its corresponding DID document have been created, the user agent 411 may update the database 416 to store a mapping relationship among the DID, an account identifier of the user, a proof of identity authentication of the user, a service ID of the user, a public key associated with the DID, a key alias associated with the user or the proof of identity authentication, other suitable information, or any combination thereof. In some embodiments, the mapping relationship may be stored in an encrypted form. To store the mapping relationship, the user agent 411 may calculate a hash value for a combination the DID and one or more items of the other identification information. In some embodiments, such a hash value may be stored as part of the DID document. The stored mapping relationship may allow the user agent 441 to identify the DID based on information received from the user-side system 310. In some embodiments, the user agent 411 may receive a request associated with the obtained DID, wherein the request comprises the account identifier and then identify the obtained DID based on the mapping relationship between the account identifier and the obtained DID. In other embodiments, the user agent 441 may receive a request for a proof of identity authentication, wherein the request comprises a DID and then locate the proof of identity authentication based on the mapping relationship between the proof of identity authentication and the DID. In some embodiments, the user agent 411 may store a recovery key for recovering the private key corresponding to the DID in association with identification information of the user. In this manner, the user agent 411 may allow the user to take control over the DID using the recovery key. Then, at step 1144, the user agent 411 may send information associated with the DID to the server 311, which may send a notification to the user at step 1146 to inform the user of the successful creation of the DID.

Figure 12:
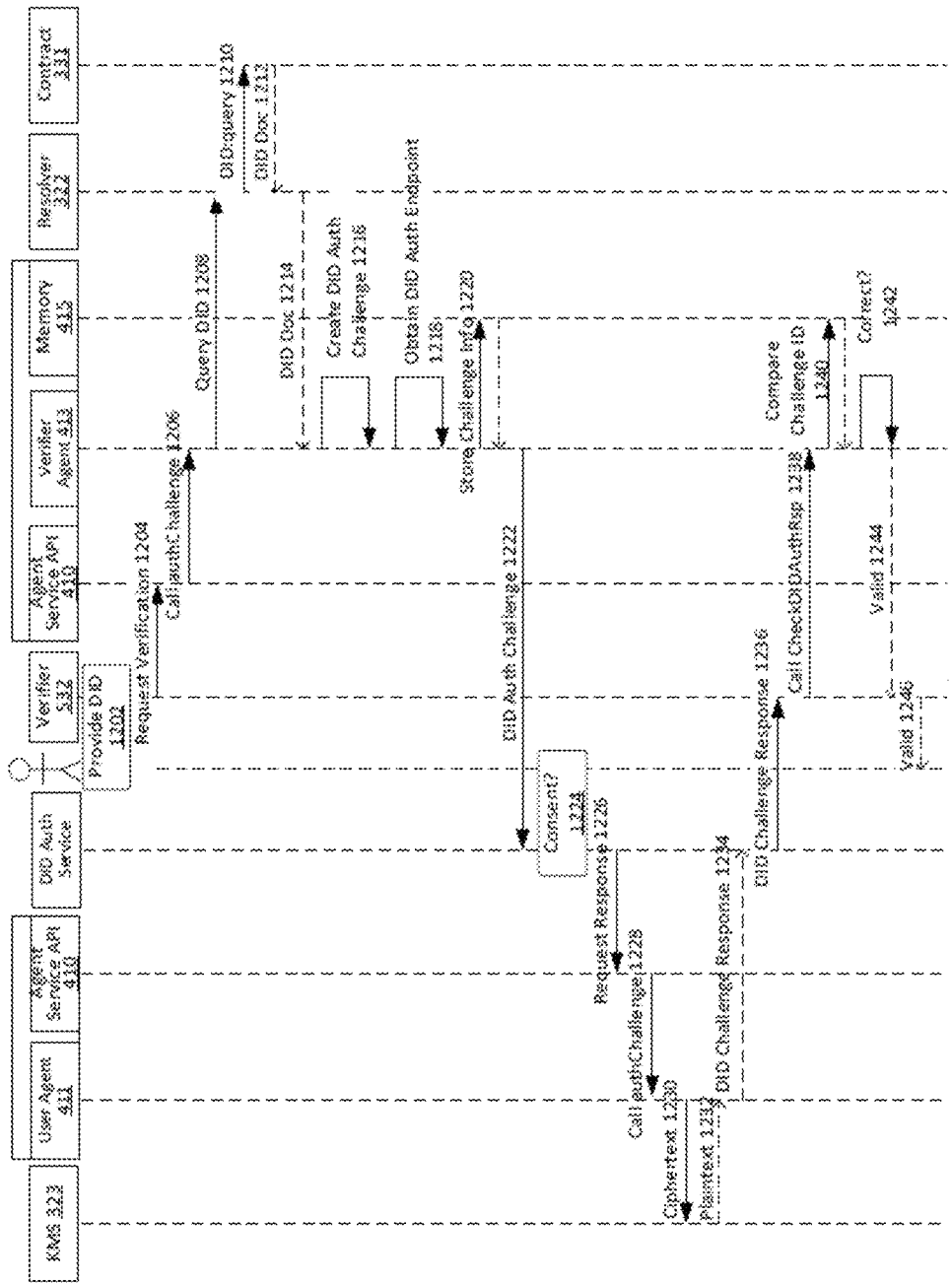
FIG. 12 illustrates a method for authenticating a decentralized identifier using an agent service in accordance with some embodiments.

FIG. 12 illustrates a method for authenticating a decentralized identifier using an agent service in accordance with some embodiments. The operations of the method presented below are intended to be illustrative. Depending on the implementation, the method may include additional, fewer, or alternative steps performed in various orders or in parallel. In some embodiments, a party (e.g., verifier) may desire to authenticate that another party (e.g., purported owner of DID) is the true owner of a DID. The authentication process may be facilitated by agent services 321 available to both parties.

In some embodiments, at step 1202, the verifier 532 may obtain a DID provided by a purported owner. At step 1204, the verifier 532 may send a request to an agent service API 410 for creating a DID authentication challenge. The request may comprise the DID to be authenticated and a network address (e.g., a URL) to which a response to the challenge is to be sent. The network address may be accessible to the verifier 532. At step 1206, the request may be forwarded from the agent service API 410 to a verifier agent 413 configured to perform operations related to authentication of DIDs. At step 1208, the verifier agent 413 may send a query to a resolver 322 for the DID document associated with the DID to be authenticated. At step 1210, the resolver 322 may formulate a transaction invoking a blockchain contract 331 for managing DIDs and send the transaction to one or more blockchain nodes associated with the blockchain 330 for execution. As a result, the resolver 322 may obtain the DID document corresponding to the DID at step 1212 and forward it to the verifier agent 413 at step 1214. At step 1216, the verifier agent 413 may create a DID authentication challenge based on the obtained DID document. In some embodiments, the DID authentication challenge may comprise a ciphertext created by encrypting original text using a public key associated with the DID that is recorded in the DID document. The challenge may also comprise the network address associated with the verifier, to which a response is to be sent. At step 1218, the verifier agent 413 may obtain information associated with the authentication service endpoint for the DID from the DID document. At step 1220, the verifier agent 413 may store an identifier of the challenge in relation to information associated with the challenge in a memory using a key-value structure. For example, the verifier agent 413 may store a challenge ID associated with the challenge in association with the DID to be authenticated, a plaintext used to create the cyphertext, and the network address for sending the response to the challenge. At step 1222, the verifier agent 413 may send the challenge to the DID authentication services associated with the DID based on information from the DID document.

In some embodiments, after obtaining the DID authentication challenge from the verifier agent 413, the DID authentication services may obtain consent from the owner of the DID for responding to such a challenge at step 1224. If the owner provides consent or permission for the identity authentication, the DID authentication services may send a request to an agent service API 410 associated with a user agent 411 for a response to the DID authentication challenge at step 1226. At step 1228, the agent service API 410 may call a corresponding functionality of the user agent 411 for creation of a response to the challenge. The response to the challenge may require restoration of the plaintext used to create the ciphertext included in the challenge using a private key associated with the DID to be authenticated. At step 1230, the user agent 411 may send the cyphertext from the challenge to the KMS 323 for decryption along with identification information associated with the DID that is recognized by the KMS 323. The KMS 323 may store a plurality of public-private key pairs in association with identification information for accounts or DIDs corresponding to the key pairs. Based on the identification information received from the user agent 411, the KMS 323 may identify the public-private key pair associated with the DID. In some embodiments, the KMS 323 may store the public key and an encrypted version of the private key. It may send the encrypted private key to a TEE associated with the KMS 323 for decryption. The private key may then be used to decrypt the ciphertext within the TEE. At step 1232, the user agent 411 may obtain the decrypted plaintext from the KMS 323.

At step 1234, the user agent 411 may generate a response to the challenge using the plaintext and send the response back to the DID authentication services. The response may comprise a challenge identifier that was contained in the original challenge. At step 1236, the DID authentication services may send the response to the network address provided by the verifier 532. Then, at step 1238, the verifier 532 may forward the response to the verifier agent 413 for checking. The verifier agent 413 may first compare the challenge identifier in the response with one or more challenge identifiers stored in the memory 415 to identify information associated with the challenge corresponding to the response at step 1240. Then at step 1242, the verifier agent 413 may determine if the purported owner of the DID is the actual owner. In some embodiments, the verifier agent may determine if the plaintext contained in the response is identical to the plaintext used to create the ciphertext in the challenge. If so, the verifier agent 413 may determine that authentication is success. The verifier agent 413 may send a confirmation message to the verifier at step 1244, which may forward the confirmation message to the owner of the DID at step 1246.

Figure 13:
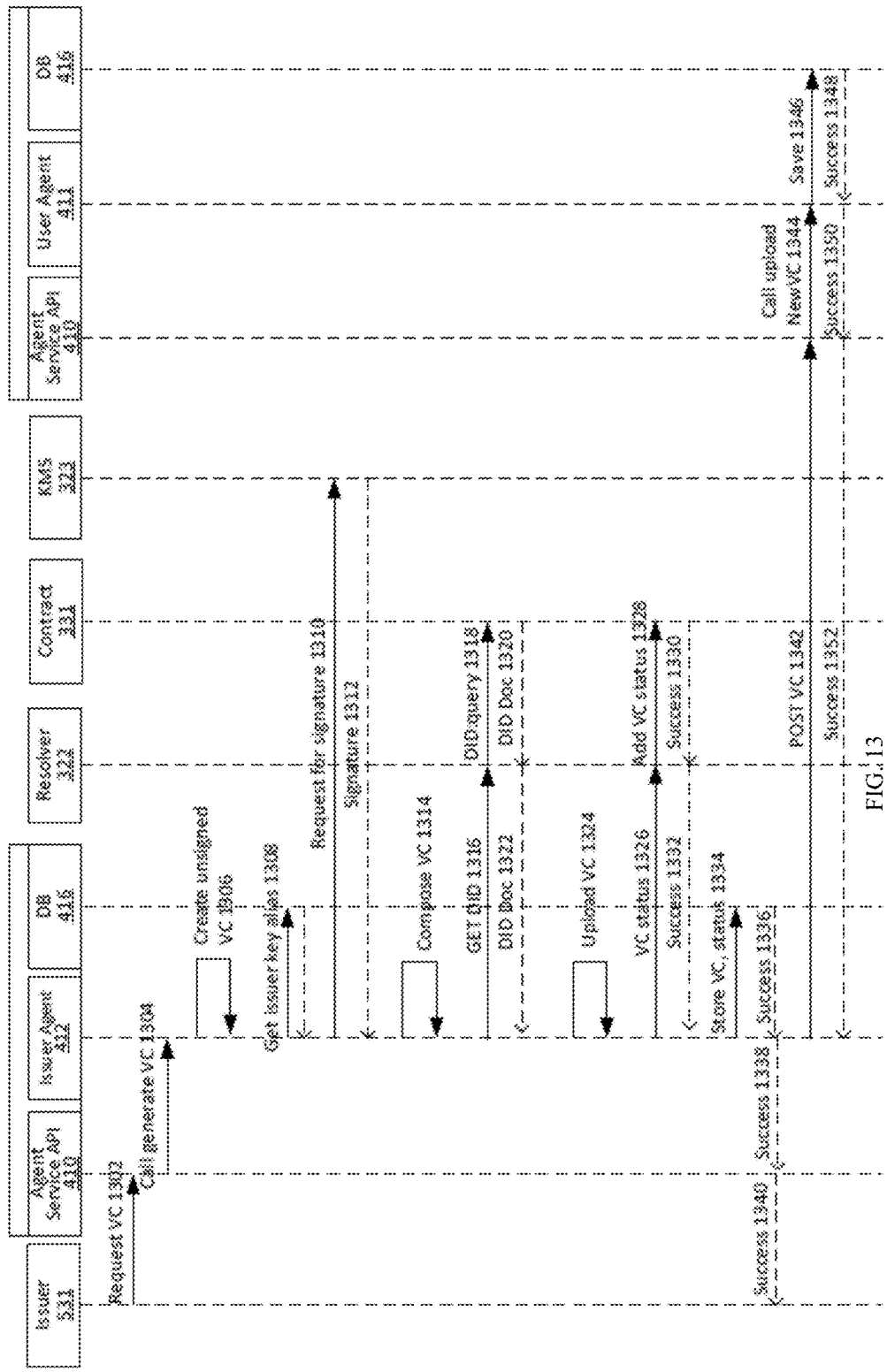
FIG. 13 illustrates a method for issuing a verifiable claim using an agent service in accordance with some embodiments.

FIG. 13 illustrates a method for issuing a verifiable claim using an agent service in accordance with some embodiments. The operations of the method presented below are intended to be illustrative. Depending on the implementation, the method may include additional, fewer, or alternative steps performed in various orders or in parallel. In some embodiments, a first entity (e.g., an issuer) may desire to issue a VC for a second entity (e.g., a user) to testify as to a fact related to the second entity. The process of issuing the VC may be facilitated by agent services 321 available to the entities.

In some embodiments, an agent service API 410 may receive, from the issuer 531, a request for creating an unsigned VC for a DID associated with the user at step 1302. At step 1304, the agent service API 410 may call the issuer agent 412 to execute operations to generate a new VC. At step 1306, the issuer agent 412 may create a VC based on the request received from the issuer 531. The VC may comprise a message that is included in the request. In some embodiments, the VC may comprise an encrypted version of the message for confidentiality reasons. The message may comprise a claim or statement regarding the user or other suitable information or data that may be conveyed to a party with access to the VC. In some embodiments, the VC may comprise a claim corresponding to identity authentication of the user (e.g., real-name authentication, real-person authentication). The request may comprise a DID of the user. The issuer agent 412 may directly create the VC based on the DID. Alternatively, the request may comprise an account identifier associated with the user (e.g., the user's account with the entity issuing the VC). In this case, the issuer agent 412 may obtain an account identifier associated with the user from the request and identify a DID based on a pre-stored mapping relationship between the account identifier and the DID. The issuer agent 412 may then create the unsigned VC based on the identified DID. The issuer agent 412 may also calculate a hash value of the content of the unsigned VC.

In some embodiments, the issuer agent 412 may obtain, in response to receiving the request, a digital signature associated with the issuer. In some embodiments, the digital signature may be obtained from the KMS 323. The issuer agent 412 may determine a key alias associated with the issuer 531 at step 1308. At step 1310, the issuer agent 412 may send a request to the KMS 323 for a digital signature associated with the issuer 531 on the VC. The request may comprise the key alias, which may be used for identification of the cryptographic keys associated with the issuer 531. The request may also comprise the hash value of the unsigned VC created by the issuer agent 412. The KMS 323 may store a plurality of public-private key pairs in association with key aliases for entities or users. Based on the key alias received from the issuer agent 412, the KMS 323 may identify the public-private key pair associated with the issuer 531. In some embodiments, the KMS 323 may store the public key and an encrypted version of the private key. It may send the encrypted private key to a TEE associated with the KMS 323 for decryption. The private key may then be used to create a digital signature of the issuer on the VC. The digital signature may be created by encrypting the hash value of the unsigned VC using the private key. At step 1312, the digital signature may be sent back to the issuer agent 412. Then, the issuer agent 412 may combine the unsigned VC with the digital signature to compose a signed VC at step 1314. In this manner, the signed VC is generated based on the request received from the issuer 531 and the digital signature.

In some embodiments, the issuer agent 412 may upload the VC to a service endpoint associated with the DID of the user or the holder of the VC. The issuer agent 412 may identify the service endpoint based on the DID document associated with the DID. At step 1316, the issuer agent 412 may send a query to a resolver 322 for the DID document associated with the DID for which the VC is issued. At step 1318, the resolver 322 may formulate a transaction invoking a blockchain contract 331 for managing DIDs and send the transaction to one or more blockchain nodes associated with the blockchain 330 for execution. The transaction may comprise information associated with the DID and may be for retrieving a DID document corresponding to the DID. As a result, the resolver 322 may obtain the DID document corresponding to the DID at step 1320 and forward it to the SDK 312 at step 1322. Based on the DID document, the issuer agent 412 may obtain information (e.g., a network address) associated with a service endpoint (e.g., a VC repository 414) for the DID from the DID document. At step 1324, the issuer agent 412 may upload the VC to the service endpoint.

In some embodiments, the issuer agent 412 may store a status of the VC. The status of the VC may be stored in a blockchain 330. In some embodiments, the blockchain 330 may be used by a service endpoint associated with the issuer 531 of the VC. At step 1326, the issuer agent 412 may send a status (e.g., valid, invalid) of the VC and a hash value of the VC to the resolver 322 for storing in the blockchain 330. At step 1328, the resolver 322 may generate and send to a blockchain node of the blockchain 330 associated with the service endpoint, a blockchain transaction for adding information associated with the VC to the blockchain. The information may comprise the status and the hash value of the VC. In some embodiments, the blockchain transaction may invoke a blockchain contract 331 for managing VCs. After sending the transaction to the blockchain node, the resolver 322 may determine that the hash value and status of the VC have been successfully stored at step 1330 and may send a confirmation to the issuer agent 412 at step 1332. In some embodiments, the status of the VC may also be stored locally. At step 1334, the issuer agent 412 may store the VC and its status at a database 416. The issuer agent 412 may receive a confirmation of successful storage at step 1336, send a confirmation to the agent service API 410 at step 1338, which may then send a confirmation to the issuer 531 indicating that the VC has been successfully created at step 1340. The confirmation to the issue may comprise the VC that has been created.

In some embodiments, the VC may be provided to the user or the holder of the VC. At step 1342, the issuer agent 412 may send the VC and/or a status of the VC to an agent service API 410 associated with a user agent 411 for the holder of the VC. The agent service API 410 may call the user agent 411 to upload the VC at step 1344. Here, the user agent 411 may serve as a service endpoint for the DID of the holder of the VC. The user agent 411 may be implemented on the same physical system as the issuer agent 412. The user agent 411 may save the VC to a database 416 at step 1346. After successful saving of the VC, the database 416 may return a success confirmation to the user agent 411 at step 1348. The user agent 411 may send a confirmation to the agent service API 410 at step 1350, which may forward a confirmation to the issuer agent 412 at step 1352.

Figure 14:
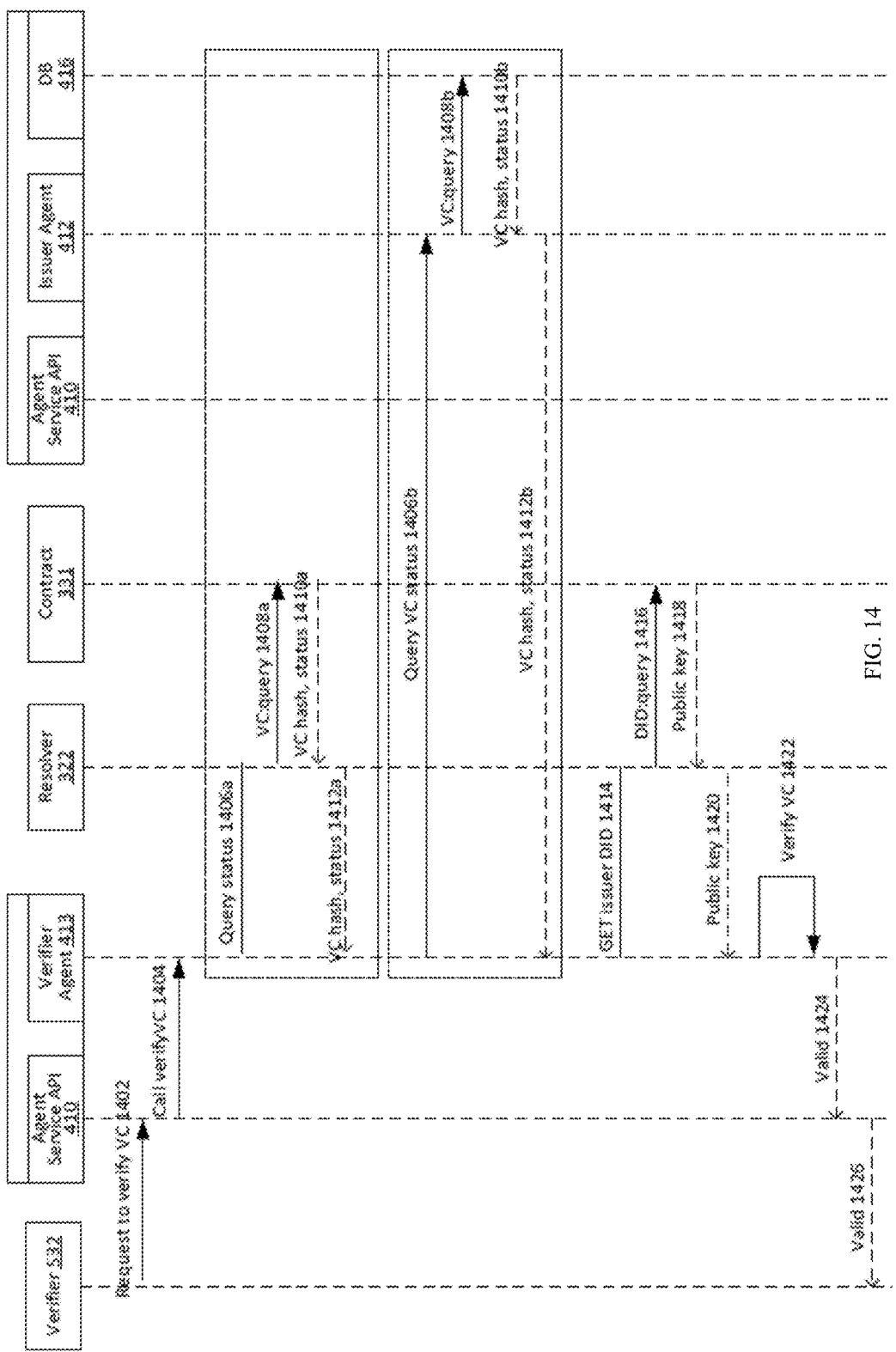
FIG. 14 illustrates a method for verifying a verifiable claim using an agent service in accordance with some embodiments.

FIG. 14 illustrates a method for verifying a verifiable claim using an agent service in accordance with some embodiments. The operations of the method presented below are intended to be illustrative. Depending on the implementation, the method may include additional, fewer, or alternative steps performed in various orders or in parallel. In some embodiments, a holder of a VC (or a subject of the VC) may present to a first entity (e.g., verifier) a VC issued by a second entity (e.g., issuer of the VC). The verifier may verify the VC with the aid of agent services 321.

In some embodiments, an agent service API 410 may receive from a verifier 532 a request to verify a VC at step 1402. The VC may comprise a digital signature associated with an issuer of the VC. At step 1404, the agent service API 410 may call a function of the verifier agent 413 for verifying the VC. In some embodiments, the verifier 532 may have directly obtained the VC from the holder of the VC. Alternatively, the verifier 532 may only have received an account identifier associated with a subject of the VC. The verifier 532 may obtain the VC by obtaining a DID associated with the subject of the VC based on a pre-stored mapping relationship between the account identifier and the DID, obtaining a DID document associated with the DID, obtaining information associated with a service endpoint for managing VCs from the DID document, and obtaining the VC from the service endpoint.

In some embodiments, the verifier agent 413 may verify a status of the VC. The verifier agent 413 may obtain and verify the status using either steps 1406a, 1408a, 1410a, and 1412a or steps 1406b, 1408b, 1410b, and 1412b. In some embodiments, the verifier agent 413 may obtain the status of the VC from a blockchain storing information associated with a plurality of VCs. At step 1406a, the verifier agent 413 may send to a resolver 322 a query for a status of the VC. The query may comprise an identifier of the VC. At step 1408a, the resolver 322 may create a blockchain transaction for retrieving a hash value and a status of the VC and send it to one or more blockchain nodes associated with a blockchain 300. The blockchain transaction may comprise a DID of the subject of the VC and may invoke a blockchain contract 331 for managing VCs. At step 1410a, the resolver 322 may obtain a status of the VC as well as a hash value associated with the VC from the blockchain 330. The resolver 322 may then send the hash value and status to the verifier agent 413 at step 1412a for verification. The verifier agent 413 may calculate a hash value by applying a hash function on the VC that was provided by the holder. The verifier agent 413 may authenticate the received status of the VC by comparing the hash value received from the blockchain 330 with the calculated hash value. If they are identical, the verifier agent 413 may determine that the received status does correspond to the VC. If the status indicates that the VC is valid, the verifier agent 413 may complete this step of the verification.

In some embodiments, the verifier agent 413 may obtain the status of the VC from a service endpoint associated with the VC. In some embodiments, the service endpoint may correspond to an issuer agent 412 associated with the issuer. At step 1406b, the verifier agent 413 may send a query to the issuer agent 412 for status of the VC. The issuer agent 412 may query the database 416 for the status of the VC at step 1408b and obtain a status and a corresponding hash value of the VC at step 1410b. The issuer agent 412 may send the hash value and the status to the verifier agent 413 at step 1412b. The verifier agent 413 may authenticate the status and verify that the VC is valid in the manner discussed above.

In some embodiments, the verifier agent 413 may determine that the VC is issued by the issuer identified on the VC. The verifier agent 413 may obtain, based on the VC, a public key associated with the issuer. The verifier agent 413 may identify the issuer based on an identifier in the VC. In some embodiments, the identifier may comprise a DID of the issuer. The public key may be obtained from the blockchain 330 based on the DID of the issuer. At step 1414, the verifier agent 413 may send a request to the resolver 322 for the public key associated with the issuer. The request may comprise the DID of the issuer. At step 1416, the resolver 322 may create a blockchain transaction invoking a blockchain contract 331 for retrieving a public key or a DID document based on a DID and send the blockchain transaction to a blockchain node of the blockchain 330. The resolver 322 may obtain the public key (e.g., by retrieving from the DID document) at step 1418 and forward the public key to the verifier agent 413 at step 1420. Then, at step 1422, the verifier agent 413 may verify the VC using the public key by determining that the digital signature is created based on a private key associated with the public key. In some embodiments, the verifier agent 413 may verify one or more other facts about the VC. For example, the verifier agent 413 may obtain, from the VC, an issuance date of the VC and validate the obtained issuance date based on a comparison between the obtained issuance date and a current date. As another example, the verifier agent 413 may obtain, from the VC, an expiration date of the VC and validate that the VC has not expired based on the expiration date and a current date. If verification of the VC is successful, the verifier agent may send a confirmation to the agent service API 410 at step 1424. The agent service API 410 may send a message to the verifier 532 confirming that the VC is verified at step 1426.

Figure 15:
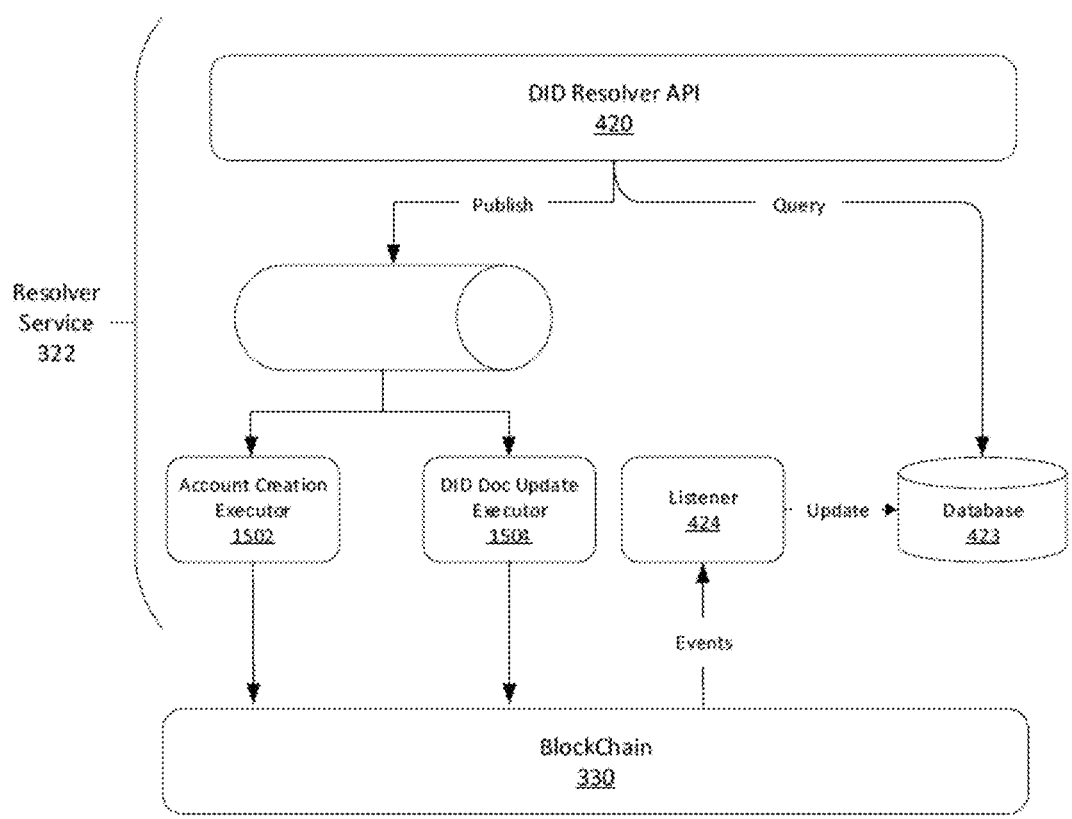
FIG. 15 illustrates a structure of a resolver in accordance with some embodiments.

FIG. 15 illustrates a structure of a resolver in accordance with some embodiments. In some embodiments, a resolver 322 may comprise a resolver API 420 for receiving requests (e.g., API calls) from systems external to the resolver 322. The requests may be directed to various functionalities of the resolver 322. The functionalities may be categorized into publishing information on a blockchain 330 and querying for information from the blockchain 330. The resolver 322 may comprise one or more executors (e.g., an account creation executor 1502, a DID document update executor 1504) for publishing information to a blockchain 330. An executor may be a software component of the resolver 322. The resolver 322 may comprise a listener 424 for querying for and acquiring information from the blockchain 330 and a database 423 for storing information acquired by the listener 424. In some embodiments, the listener 424 may be a software component of the resolver 322 that may periodically check for transactions associated with newly-created blocks or new events in the blockchain 330, determine transactions or events that are related to DIDs and VCs managed by the resolver 322, and store the updates in the database 423 for use. In some embodiments, the resolver 322 may directly communicate with one or more blockchain nodes associated with the blockchain 330. Alternatively or additionally, the resolver 322 may communicate with the blockchain 330 via one or more software interfaces such as a BaaS cloud 324.

After a request is received via the resolver API 420, the resolver 322 may direct the request to one or more components of the resolver 322 for processing. In some embodiments, the resolver 322 may receive one or more requests associated with publishing information to a blockchain 330. As an example, the resolver 322 may receive a request for creating a new DID via the resolver API 420. The resolver 322 may direct this request to the account creation executor 1502. The account creation executor 1502 may send one or more blockchain transactions for creating the DID to one or more blockchain nodes associated with the blockchain 330 for execution. The blockchain transactions may comprise a blockchain transaction for creating a new account on the blockchain 330. An identifier of the new account may be used to create the DID. In some embodiments, after the DID is created, the DID document update executor 1504 may be invoked to send, to one or more blockchain nodes associated with the blockchain 330 for execution, one or more blockchain transactions for adding a DID document associated with the DID. As another example, the resolver 322 may receive a request for updating a DID document via the resolver API 420. The resolver 322 may direct this request to the DID document update executor 1504. The DID document update executor 1504 may generate one or more blockchain transactions for updating the DID document based on the request and send the one or more blockchain transactions to one or more blockchain nodes associated with the blockchain 330 for execution.

In some embodiments, the resolver 322 may receive one or more requests querying for information from the blockchain 330. As an example, the resolver 322 may receive a query for a DID document via the resolver API 420. The query may comprise a DID, for which the DID document is requested. The resolver 322 may generate and send, to one or more blockchain nodes associated with the blockchain 330 for execution, one or more blockchain transactions for identifying the DID document based on the DID. The resolver 322 may then obtain the DID document from the blockchain 330 and return the DID document to a sender of the request. As another example, the resolver 322 may receive a query for a public key associated with a DID via the resolver API 420. The resolver 322 may generate and send, to one or more blockchain nodes associated with the blockchain 330 for execution, one or more blockchain transactions for accessing a DID document containing the public key based on the DID. The resolver 322 may obtain the public key from the blockchain 330 and return the public key to a sender of the request.

Figure 16:
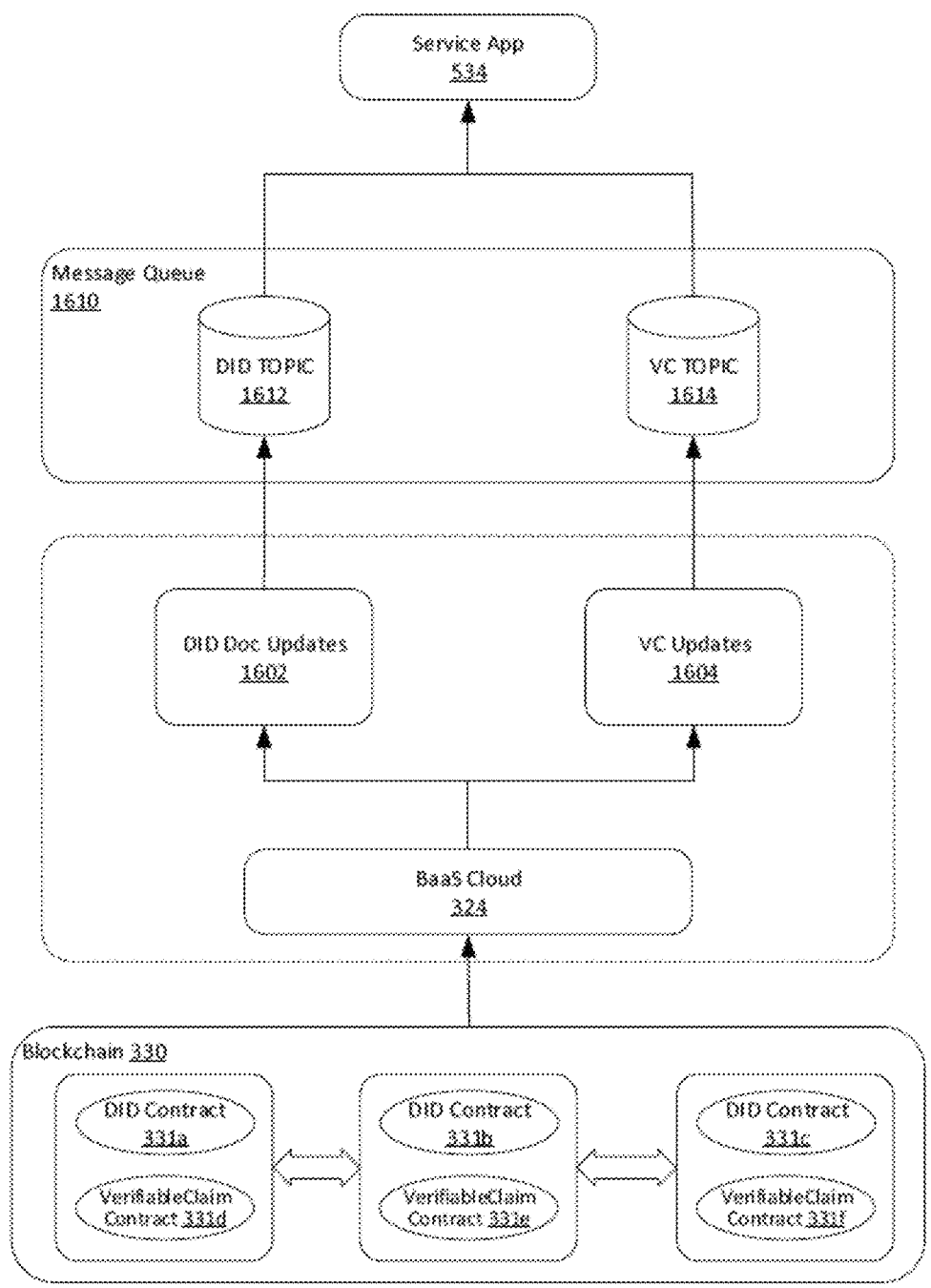
FIG. 16 illustrates a system for synchronizing event information associated with decentralized identifiers or verifiable claims from a blockchain to an application in accordance with some embodiments.

FIG. 16 illustrates a system for synchronizing event information associated with decentralized identifiers or verifiable claims from a blockchain to an application in accordance with some embodiments. In some embodiments, a resolver 322 may act as an intermediary and create a data channel between a blockchain 330 for managing DIDs and VCs and one or more service applications 534 that make use of information associated with the DIDs and VCs. In some embodiments, the data channel created by the resolver 322 may be used for synchronization between local databases maintained by entities providing the service applications 534 and data stored in the blockchain. In some embodiments, the resolver 322 may support the synchronization by feeding or pushing relevant data from the blockchain 330 to the service applications 534. In some embodiments, the resolver 322 may communicate with one or more blockchain nodes of the blockchain 330 via a software interface or platform (e.g., a BaaS cloud 324).

In some embodiments, the resolver 322 may obtain data stored in new blocks added to the blockchain 330 via the BaaS cloud 324. The data may comprise a plurality of blockchain transactions stored on the blockchain 330, which may include one or more blockchain transactions related to DIDs or VCs. In some embodiments, such blockchain transactions may be identified based on one or more blockchain contracts 331 that they are associated with. Data associated with the blockchain transactions may be categorized into, for example, one or more updates associated with DID documents and one or more updates associated with VCs. The data may be published into a message queue 1610 that may include a DID topic message queue 1612 and a VC topic message queue 1614. The message queue 1610 may be supported by a message broker or queue messenger platform or service. The message broker may receive a plurality of messages from a message producer (e.g., the resolver 322) and deliver the messages to one or more consumers (e.g., a service application 534). In some embodiments, the service application 534 may subscribe to and receive a portion of messages from the DID topic message queue 1612 or the VC topic message queue 1614. The service application 534 may subscribe to messages or updates related to DIDs associated with accounts maintained by the service application 534.

Figure 17:
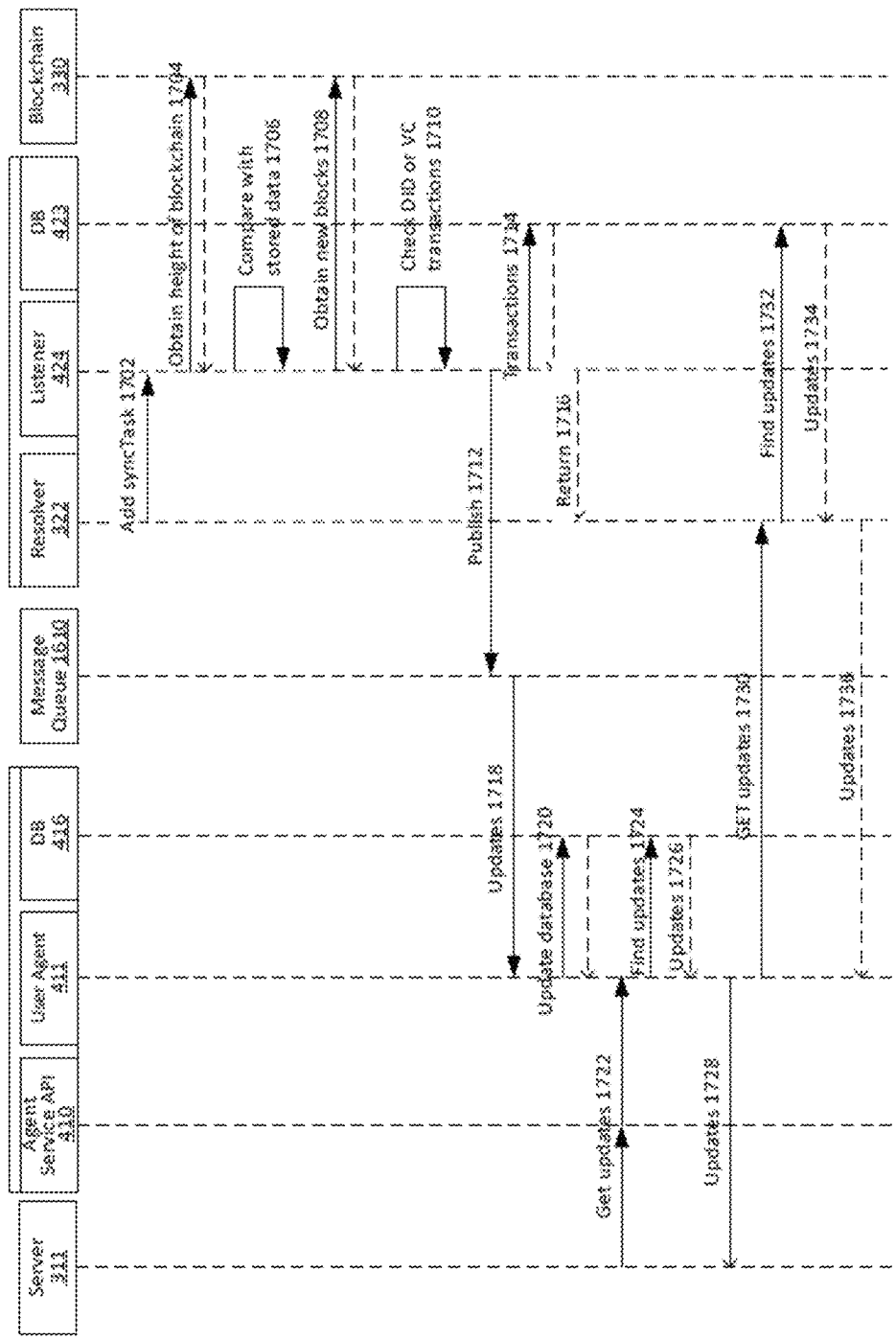
FIG. 17 illustrates a method for obtaining updates associated with decentralized identifiers or verifiable claims from a blockchain in accordance with some embodiments.

FIG. 17 illustrates a method for obtaining updates associated with decentralized identifiers or verifiable claims from a blockchain in accordance with some embodiments. The operations of the method presented below are intended to be illustrative. Depending on the implementation, the method may include additional, fewer, or alternative steps performed in various orders or in parallel. In some embodiments, the resolver 322 may obtain information associated with one or more DIDs or VCs from a blockchain 330 and provide updates to a server 311. The server 311 may be associated with a user-side system 310 that provides services based on information associated with DIDs or VCs. In some embodiments, on a periodic basis or at points of time chosen in a suitable manner, the resolver 322 may access an up-to-date version of the blockchain 330 and obtain event data from the blockchain 330. The event data may comprise a plurality of updates associated with a plurality of DID documents stored on the blockchain 330 and/or a plurality of updates associated with a plurality of VCs.

In some embodiments, the resolver 322 may send a synchronization task to its listener 424 at step 1702 to initiate the process of obtaining updates. The listener 424 may obtain new data in the blockchain 330 that has not been previously accessed or stored by the resolver 322. Data from the blockchain 330 may be stored in the database 423 associated with the resolver 322. At step 1704, the listener 424 may obtain a current height of the blockchain 330. The height of a block in the blockchain 330 may be defined as the number of blocks preceding the block on the blockchain 330. The height of the blockchain 330 may equal the height of the newest block in the blockchain 330. At step 1706, the listener 424 may compare the obtained current height of the blockchain with a maximum height in the blockchain that data currently stored in the database 423 corresponds to. The database 423 may store a full copy of the blockchain 330, a portion of the blockchain 330, or data from various parts of the blockchain 330. To determine the maximum height value, the listener 424 may identify the blocks in the blockchain 330 that contain the data stored in the database 423 and find the block with the largest height among the identified blocks. The height of this block in the blockchain 330 would be the maximum height. If this maximum height of stored data is smaller than the current height of the blockchain 330. The listener 424 may determine that new data has been added to the blockchain and an update to the database 423 is needed. At step 1708, the listener may obtain a plurality of blocks from the blockchain. Each of the obtained blocks may correspond to a height in the blockchain greater than the maximum height. In other words, the obtained blocks are blocks newly added to the blockchain 330 that have not been stored by the resolver 322.

In some embodiments, the resolver 322 may filter the event data obtained from the blockchain 330 to identity those that are related to DIDs, DID documents, or VCs. At step 1710, the listener 424 may search, in the obtained new blocks, for transactions involving one or more blockchain contracts 331 associated with DIDs or VCs. One or more of the transactions in the newly-created blocks may be inputs or outputs to one or more blockchain contracts 331 and may thus comprise identifiers of their corresponding blockchain contracts 331. The resolver 322 may identify transactions of interest based on their inclusion of identifiers of blockchain contracts associated with, for example, creation of DIDs, updating of DID documents, updating of VC status, other operations, or any combination thereof. The resolver 322 may thereby collect one or more inputs and outputs associated with the blockchain contracts associated with DIDs or VCs. The resolver 322 may further identify one or more of the transactions that are related to updates to information stored on the blockchain 330 that are related to one or more DIDs, DID documents, or VCs. At step 1712, the listener 424 may publish the obtained transactions or data thereof to the message queue 1610. At step 1714, the listener 424 may store event data in the database 423. At step 1716, the listener 424 may return a message to the resolver 322 confirming that the synchronization task is completed.

In some embodiments, the message queue 1610 may provide updates to a user agent 411 used by a user-side system 310. A message broker application associated with the message queue 1610 may send a plurality of updates at step 1718 to the user agent 411. At 1720, the user agent 411 may update a local database 416 based on the updates received from the message queue 1610. As an example, the user agent 411 may update a structural database storing statuses of DID documents in association with their corresponding DIDs based on the received updates.

In some embodiments, the user agent 411 may provide the updates to a user-side system 310. As an example, at step 1722, the user agent 411 may receive a request from a server 311 associated with the user-side system 310 for updates associated with one or more DIDs, DID documents, or VCs via an agent service API 410. The user agent 411 may query the database 416 for such updates at step 1724 and obtain the updates at step 1726. At step 1728, the user agent 411 may send the requested updates to the server 331.

In some embodiments, the resolver 322 may directly provide the user agent 411 with updates associated with one or more DIDs or VCs without using the message queue 1610. As an example, at step 1730, the resolver 322 may receive a request for information associated with event data obtained from the blockchain 330. The requested information may comprise updates associated with one or more DIDs, DID documents, or VCs. In some embodiments, the request may comprise one or more account identifiers associated with a user-side system 310. One or more DIDs may be identified based on pre-stored mapping relationships between account identifiers and DIDs. Then, information associated with event data about the DIDs may be identified and provided. The resolver 322 may query the database 423 for the requested information at step 1732 and obtain the requested information at step 1734. At step 1736, the resolver 322 may send the requested information to the user agent 411. In some embodiments, the resolver 322 may provide information about one or more updates associated with one or more DID documents or VCs to the user agent 411 or other suitable agent services or software configured to manage DIDs or VCs for a plurality of users. Alternatively, the resolver 322 may provide such information directly to an external system, such as the server 311.

In some embodiments, by using the message queue 1610 to deliver information associated with blockchain events and saving such information in a local database 423, the resolver may provide the event information in an efficient and low-cost manner to systems using such information (e.g., agent services 321, user-side systems 310). The systems using such information is relieved of the burden of accessing information or performing operations on the blockchain 330. Rather, the resolver 322 may performing operations in association with the blockchain 330 and obtain event and update information in batches. The entities may directly acquire needed information from the resolver 322 and its database 423.

Figure 18:
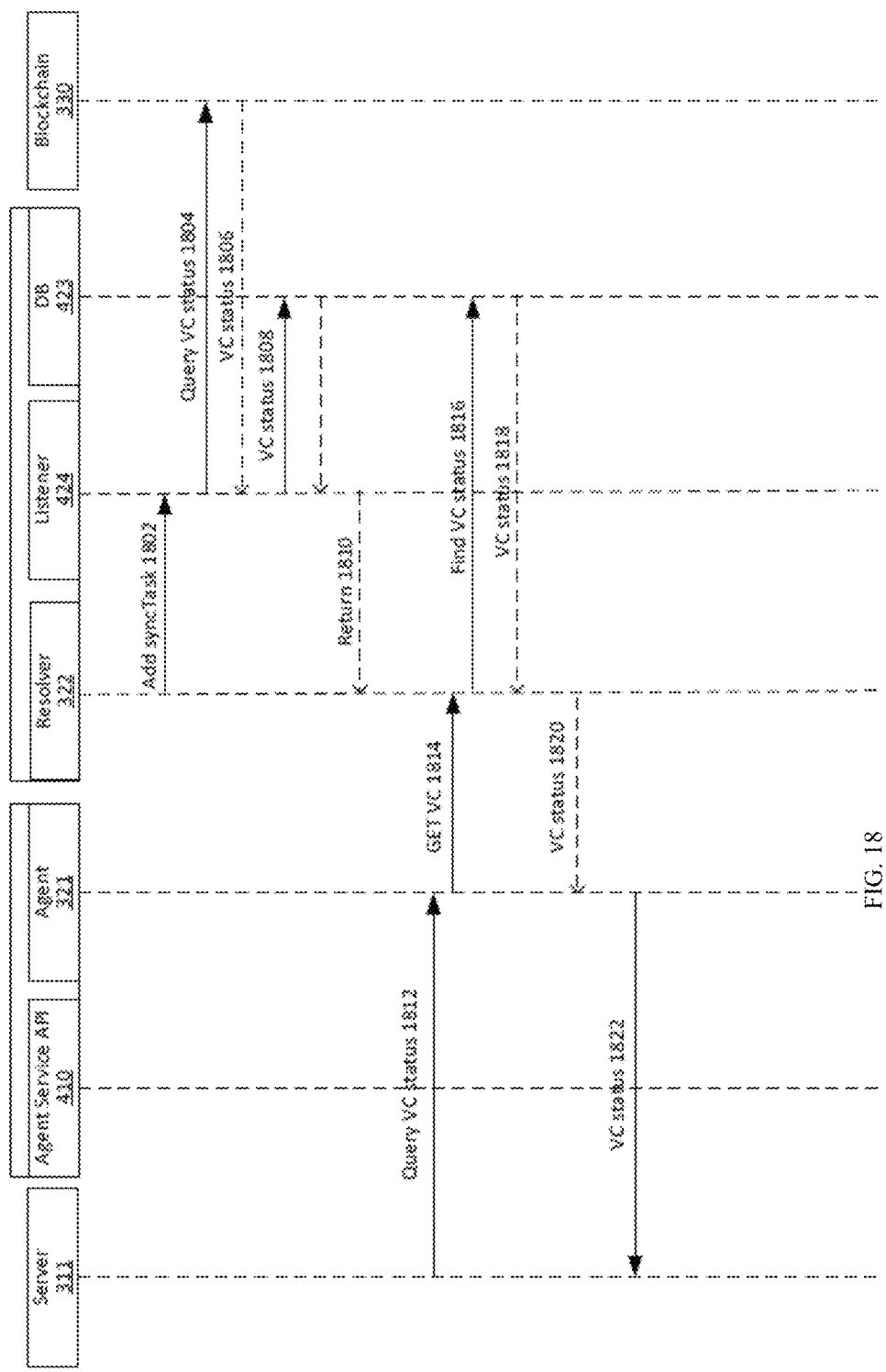
FIG. 18 illustrates a method for obtaining status of a verifiable claim from a blockchain in accordance with some embodiments.

FIG. 18 illustrates a method for obtaining status of a verifiable claim from a blockchain in accordance with some embodiments. The operations of the method presented below are intended to be illustrative. Depending on the implementation, the method may include additional, fewer, or alternative steps performed in various orders or in parallel. In some embodiments, status associated with one or more VCs may be stored on a blockchain 330. The resolver 322 may obtain information associated with the VC status from the blockchain 330 and provide it to one or more other systems. In some embodiments, the resolver 322 may send a synchronization task to a listener 424 at step 1802 to start the process of obtaining status of VCs from the blockchain. The listener 424 may query data stored in the blockchain 330 for such status at step 1804. In some embodiments, the listener 424 may send, to one or more blockchain nodes associated with the blockchain 330 for execution, one or more blockchain transactions for obtaining the status of the VCs. The blockchain transactions may comprise one or more identifiers associated with the VCs that are subjects of the query. The blockchain transactions may invoke one or more blockchain contracts configured to manage correspondence relationships between the identifiers and the status of the VCs. At step 1806, the listener 424 may obtain status information for the one or more VCs. The listener 424 may further obtain a hash value associated with each of the VCs in relation to the status information. The hash values may be used for verification purposes as described herein. At step 1808, the listener 424 may update the database 423 based on the obtained status information. At step 1810, the listener 424 may return a message to the resolver 322 confirming that the synchronization task has been completed. In some embodiments, the resolver 322 may also obtain status information of a VC in response to a request. The resolver 322 may receive a query for information associated with a VC. The query may comprise one or more identifiers for the VC. In response, the resolver 322 may send, to a blockchain node of the blockchain 330, a blockchain transaction for accessing the information associated with the VC based on the one or more identifiers.

In some embodiments, the resolver 322 may provide status information about one or more VCs in response to a request from the agent services 321. For example, at step 1812, a server 311 associated with a user-side system 310 may send a request to the agent 321 querying for status of a VC. At step 1814, the agent 321 may send the resolver 322 a request for the queried status information. The resolver 322 may search the database 423 for responsive information at step 1816 and obtain the status of the VC at step 1818. The resolver 322 may send the status information to the agent 321 at step 1820. The agent 321 may send the status information to the server 311 at step 1822.

Figure 19:
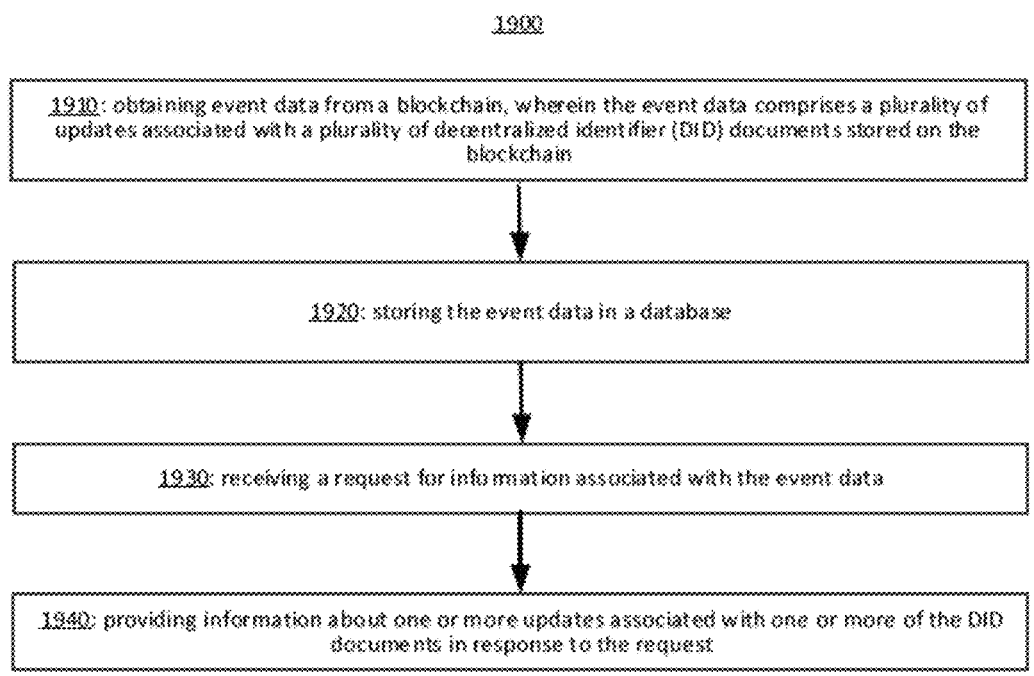
FIG. 19 illustrates a flowchart of a method for implementing a resolver service in accordance with some embodiments.

FIG. 19 illustrates a flowchart of a method for implementing a resolver service in accordance with some embodiments. The method 1900 may be performed by a device, apparatus, or system for a resolver service. The method 1900 may be performed by one or more components of the environment or system illustrated by FIGS. 1-5, 15, and 16, such as one or more components of the resolver services 322. Depending on the implementation, the method 1900 may include additional, fewer, or alternative steps performed in various orders or in parallel.

Block 1910 includes obtaining event data from a blockchain. Block 1920 includes storing the event data in a database. In some embodiments, the event data comprises a plurality of updates associated with a plurality of decentralized identifier (DID) documents stored on the blockchain. In some embodiments, the event data further comprises a plurality of updates associated with a plurality of verifiable claims (VCs). In some embodiments, the obtaining event data comprises periodically accessing an up-to-date version of the blockchain.

In some embodiments, the obtaining event data comprises obtaining a current height of the blockchain, comparing the obtained current height of the blockchain with a maximum height in the blockchain that data currently stored in the database corresponds to, and obtaining a plurality of blocks from the blockchain, wherein each of the obtained blocks corresponds to a height in the blockchain greater than the maximum height. In some embodiments, the obtaining event data further comprises searching, in the obtained blocks, for transactions involving one or more blockchain contracts associated with DIDs or VCs and collecting one or more inputs and outputs associated with the one or more blockchain contracts.

Block 1930 includes receiving a request for information associated with the event data. Block 1940 includes providing information about one or more updates associated with one or more of the DID documents in response to the request. In some embodiments, the providing information about one or more updates comprises sending the information to an online agent configured to manage DIDs or VCs for a plurality of users. In some embodiments, the receiving a request for information associated with the event data comprises receiving the request from an entity, wherein the request comprises one or more account identifiers; the providing information about one or more updates comprises identifying one or more DIDs based on pre-stored mapping relationships between a plurality of account identifiers and a plurality of DIDs and sending information associated with the identified one or more DIDs to the entity.

In some embodiments, the method further comprises receiving a request for creating a DID and sending one or more blockchain transactions for creating the DID and for adding a DID document associated with the DID to a blockchain node for execution.

In some embodiments, the method further comprises receiving a request for updating a DID document and sending a blockchain transaction for updating the DID document to a blockchain node for execution.

In some embodiments, the method further comprises receiving a query for a DID document, the query comprising a DID and sending a blockchain transaction for identifying the DID document based on the DID to a blockchain node for execution.

In some embodiments, the method further comprises receiving a query for a public key associated with a DID and sending, to a blockchain node for execution, a blockchain transaction for accessing a DID document containing the public key based on the DID.

In some embodiments, the method further comprises receiving a query for information associated with a VC, the query comprising one or more identifiers for the VC and sending, to a blockchain node for execution, a blockchain transaction for accessing the information associated with the VC based on the one or more identifiers.

Figure 20:
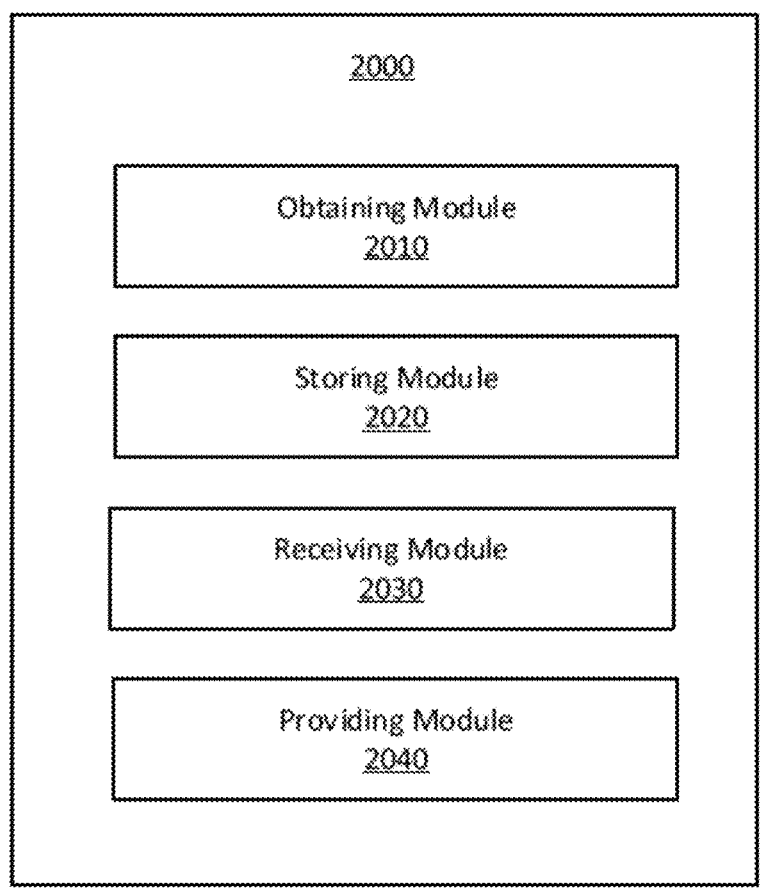
FIG. 20 illustrates a block diagram of a computer system for implementing a resolver service in accordance with some embodiments.

FIG. 20 illustrates a block diagram of a computer system for implementing a resolver service in accordance with some embodiments. The system 2000 may be an example of an implementation of one or more components of the service-side system 320 of FIG. 3 or one or more other components illustrated in FIGS. 1-5, 15, and 16. The method 1900 may be implemented by the computer system 2000. The computer system 2000 may comprise one or more processors and one or more non-transitory computer-readable storage media (e.g., one or more memories) coupled to the one or more processors and configured with instructions executable by the one or more processors to cause the system or device (e.g., the processor) to perform the above-described method, e.g., the method 1900. The computer system 2000 may comprise various units/modules corresponding to the instructions (e.g., software instructions). In some embodiments, the computer system 2000 may be referred to as an apparatus for implementing a resolver service. The apparatus may comprise an obtaining module 2010 for obtaining event data from a blockchain, wherein the event data comprises a plurality of updates associated with a plurality of decentralized identifier (DID) documents stored on the blockchain; a storing module 2020 for storing the event data in a database; a receiving module 2030 for receiving a request for information associated with the event data; and a providing module 2040 for providing information about one or more updates associated with one or more of the DID documents in response to the request.

The techniques described herein are implemented by one or more special-purpose computing devices. The special-purpose computing devices may be desktop computer systems, server computer systems, portable computer systems, handheld devices, networking devices or any other device or combination of devices that incorporate hard-wired and/or program logic to implement the techniques. The special-purpose computing devices may be implemented as personal computers, laptops, cellular phones, camera phones, smart phones, personal digital assistants, media players, navigation devices, email devices, game consoles, tablet computers, wearable devices, or a combination thereof. Computing device(s) are generally controlled and coordinated by operating system software. Conventional operating systems control and schedule computer processes for execution, perform memory management, provide file system, networking, I/O services, and provide a user interface functionality, such as a graphical user interface ("GUI"), among other things. The various systems, apparatuses, storage media, modules, and units described herein may be implemented in the special-purpose computing devices, or one or more computing chips of the one or more special-purpose computing devices. In some embodiments, the instructions described herein may be implemented in a virtual machine on the special-purpose computing device. When executed, the instructions may cause the special-purpose computing device to perform various methods described herein. The virtual machine may include a software, hardware, or a combination thereof.

Figure 21:
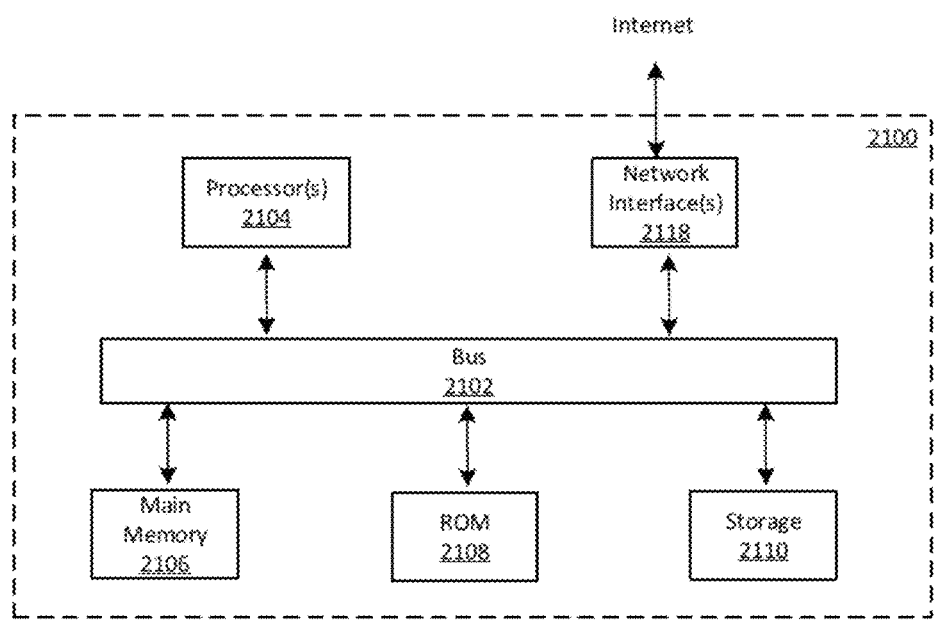
FIG. 21 illustrates a block diagram of a computer system in which any of the embodiments described herein may be implemented.

FIG. 21 illustrates a block diagram of a computer system in which any of the embodiments described herein may be implemented. The system 2100 may be implemented in any of the components of the environments or systems illustrated in FIGS. 1-5, 15, and 16. the software applications or services illustrated in FIGS. 1-5, 15, and 16 may be implemented and operated on the system 2100. One or more of the example methods illustrated by FIGS. 6-14 and 17-19 may be performed by one or more implementations of the computer system 2100.

The computer system 2100 may include a bus 2102 or other communication mechanism for communicating information, one or more hardware processor(s) 2104 coupled with bus 2102 for processing information. Hardware processor(s) 2104 may be, for example, one or more general purpose microprocessors.

The computer system 2100 may also include a main memory 2106, such as a random access memory (RAM), cache and/or other dynamic storage devices, coupled to bus 2102 for storing information and instructions executable by processor(s) 2104. Main memory 2106 also may be used for storing temporary variables or other intermediate information during execution of instructions executable by processor(s) 2104. Such instructions, when stored in storage media accessible to processor(s) 2104, render computer system 2100 into a special-purpose machine that is customized to perform the operations specified in the instructions. The computer system 2100 may further include a read only memory (ROM) 2108 or other static storage device coupled to bus 2102 for storing static information and instructions for processor(s) 2104. A storage device 2110, such as a magnetic disk, optical disk, or USB thumb drive (Flash drive), etc., may be provided and coupled to bus 2102 for storing information and instructions.

The computer system 2100 may implement the techniques described herein using customized hard-wired logic, one or more ASICs or FPGAs, firmware and/or program logic which in combination with the computer system causes or programs computer system 2100 to be a special-purpose machine. According to one embodiment, the operations, methods, and processes described herein are performed by computer system 2100 in response to processor(s) 2104 executing one or more sequences of one or more instructions contained in main memory 2106. Such instructions may be read into main memory 2106 from another storage medium, such as storage device 2110. Execution of the sequences of instructions contained in main memory 2106 may cause processor(s) 2104 to perform the process steps described herein. In alternative embodiments, hard-wired circuitry may be used in place of or in combination with software instructions.

The main memory 2106, the ROM 2108, and/or the storage device 2110 may include non-transitory storage media. The term "non-transitory media," and similar terms, as used herein refers to media that store data and/or instructions that cause a machine to operate in a specific fashion, the media excludes transitory signals. Such non-transitory media may comprise non-volatile media and/or volatile media. Non-volatile media includes, for example, optical or magnetic disks, such as storage device 2110. Volatile media includes dynamic memory, such as main memory 2106. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

The computer system 2100 may include a network interface 2118 coupled to bus 2102. Network interface 2118 may provide a two-way data communication coupling to one or more network links that are connected to one or more local networks. For example, network interface 2118 may be an integrated services digital network (ISDN) card, cable modem, satellite modem, or a modem to provide a data communication connection to a corresponding type of telephone line. As another example, network interface 2118 may be a local area network (LAN) card to provide a data communication connection to a compatible LAN (or WAN component to communicate with a WAN). Wireless links may also be implemented. In any such implementation, network interface 2118 may send and receive electrical, electromagnetic or optical signals that carry digital data streams representing various types of information.

The computer system 2100 can send messages and receive data, including program code, through the network(s), network link and network interface 2118. In the Internet example, a server might transmit a requested code for an application program through the Internet, the ISP, the local network and the network interface 2118.

The received code may be executed by processor(s) 2104 as it is received, and/or stored in storage device 2110, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another or may be combined in various ways. All possible combinations and sub-combinations are intended to fall within the scope of this specification. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The examples of blocks or states may be performed in serial, in parallel, or in some other manner. Blocks or states may be added to or removed from the disclosed embodiments. The examples of systems and components described herein may be configured differently than described. For example, elements may be added to, removed from, or rearranged compared to the disclosed embodiments.

The various operations of methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some embodiments, the processors or processor-implemented engines may be located in a single geographic location (e.g., within a home environment, an office environment, or a server farm). In other embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific embodiments, various modifications and changes may be made to these embodiments without departing from the broader scope of embodiments of the specification. The Detailed Description should not to be taken in a limiting sense, and the scope of various embodiments is defined only by the appended claims, along with the full range of equivalents to which such claims are entitled. Furthermore, related terms (such as "first," "second," "third," etc.) used herein do not denote any order, height, or importance, but rather are used to distinguish one element from another element. Furthermore, the terms "a," "an," and "plurality" do not denote a limitation of quantity herein, but rather denote the presence of at least one of the articles mentioned.

The invention claimed is:

1. A computer-implemented method, comprising:
receiving a request for updating a decentralized identifier (DID) document stored on a blockchain, wherein the request comprises an account identifier of a user account associated with a user-side system, the user-side system corresponding to a second DID;
identifying a first DID corresponding to the account identifier based on a pre-stored mapping relationship between the first DID and the account identifier, wherein the first DID corresponds to the DID document and wherein the DID document comprises the second DID;
generating, based on the identified first DID, a blockchain transaction for updating the DID document; and
sending the blockchain transaction to one or more blockchain nodes associated with the blockchain for execution.

2. The method of claim 1, wherein the receiving a request for updating a DID document comprises:
receiving, via an application programming interface (API), an API call comprising the request.

3. The method of claim 1, wherein the blockchain transaction invokes a blockchain contract associated with the blockchain, wherein the blockchain contract is executable to update the DID document.

4. The method of claim 1, further comprising:
obtaining, from the blockchain, event data of a plurality of blockchain transactions associated with the first DID, wherein the plurality of blockchain transactions comprise the blockchain transaction for updating the DID document;
storing the event data in a database; and
provisioning the event data in response to a request for information associated with the event data.

5. The method of claim 4, wherein the obtaining event data comprises periodically accessing an up-to-date version of the blockchain.

6. The method of claim 4, wherein the obtaining event data comprises:
obtaining a current height of the blockchain;
comparing the obtained current height of the blockchain with a maximum height in the blockchain that data currently stored in the database corresponds to; and
obtaining a plurality of blocks from the blockchain, wherein each of the obtained blocks corresponds to a height in the blockchain greater than the maximum height.

7. The method of claim 6, wherein the obtaining event data further comprises:
searching, in the obtained blocks, for transactions involving one or more blockchain contracts associated with the first DID; and
collecting one or more inputs and outputs associated with the one or more blockchain contracts.

8. A non-transitory computer-readable storage medium, configured with instructions executable by one or more processors to cause the one or more processors to perform operations comprising:
receiving a request for updating a decentralized identifier (DID) document stored on a blockchain, wherein the request comprises an account identifier of a user account associated with a user-side system, the user-side system corresponding to a second DID;
identifying a first DID corresponding to the account identifier based on a pre-stored mapping relationship between the first DID and the account identifier, wherein the first DID corresponds to the DID document and wherein the DID document comprises the second DID;
generating, based on the identified first DID, a blockchain transaction for updating the DID document; and
sending the blockchain transaction to one or more blockchain nodes associated with the blockchain for execution.

9. The medium of claim 8, wherein the receiving a request for updating a DID document comprises:
receiving, via an application programming interface (API), an API call comprising the request.

10. The medium of claim 8, wherein the blockchain transaction invokes a blockchain contract associated with the blockchain, wherein the blockchain contract is executable to update the DID document.

11. The medium of claim 8, wherein the operations further comprise:
obtaining, from the blockchain, event data of a plurality of blockchain transactions associated with the first DID, wherein the plurality of blockchain transactions comprise the blockchain transaction for updating the DID document;
storing the event data in a database; and
provisioning the event data in response to a request for information associated with the event data.

12. The medium of claim 11, wherein the obtaining event data comprises periodically accessing an up-to-date version of the blockchain.

13. The medium of claim 11, wherein the obtaining event data comprises:
obtaining a current height of the blockchain;
comparing the obtained current height of the blockchain with a maximum height in the blockchain that data currently stored in the database corresponds to; and
obtaining a plurality of blocks from the blockchain, wherein each of the obtained blocks corresponds to a height in the blockchain greater than the maximum height.

14. The medium of claim 13, wherein the obtaining event data further comprises:
searching, in the obtained blocks, for transactions involving one or more blockchain contracts associated with the first DID; and
collecting one or more inputs and outputs associated with the one or more blockchain contracts.

15. A system comprising a processor and a non-transitory computer-readable storage medium storing instructions executable by the processor to cause the system to perform operations comprising:
receiving a request for updating a decentralized identifier (DID) document stored on a blockchain, wherein the request comprises an account identifier of a user account associated with a user-side system, the user-side system corresponding to a second DID;
identifying a first DID corresponding to the account identifier based on a pre-stored mapping relationship between the first DID and the account identifier, wherein the first DID corresponds to the DID document and wherein the DID document comprises the second DID;
generating, based on the identified first DID, a blockchain transaction for updating the DID document; and
sending the blockchain transaction to one or more blockchain nodes associated with the blockchain for execution.

16. The system of claim 15, wherein the receiving a request for updating a DID document comprises:
receiving, via an application programming interface (API), an API call comprising the request.

17. The system of claim 15, wherein the blockchain transaction invokes a blockchain contract associated with the blockchain, wherein the blockchain contract is executable to update the DID document.

18. The system of claim 15, wherein the operations further comprise:
obtaining, from the blockchain, event data of a plurality of blockchain transactions associated with the first DID, wherein the plurality of blockchain transactions comprise the blockchain transaction for updating the DID document;
storing the event data in a database; and
provisioning the event data in response to a request for information associated with the event data.

19. The system of claim 18, wherein the obtaining event data comprises periodically accessing an up-to-date version of the blockchain.

20. The system of claim 18, wherein the obtaining event data comprises:
obtaining a current height of the blockchain;
comparing the obtained current height of the blockchain with a maximum height in the blockchain that data currently stored in the database corresponds to; and
obtaining a plurality of blocks from the blockchain, wherein each of the obtained blocks corresponds to a height in the blockchain greater than the maximum height.

* * * * *